(12) United States Patent
Yoder et al.

(10) Patent No.: US 11,315,683 B2
(45) Date of Patent: *Apr. 26, 2022

(54) FACILITATING INTEGRITY OF TELEMETRY CONNECTIVITY BETWEEN A MEDICAL DEVICE AND A REMOTE DEVICE

(71) Applicant: Medtronic, Inc., Minneapolis, MN (US)

(72) Inventors: Matthew R. Yoder, Crystal, MN (US); Bo Zhang, Blaine, MN (US); Gary P. Kivi, Maple Grove, MN (US); Richard A. Sanden, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/722,286

(22) Filed: Dec. 20, 2019

(65) Prior Publication Data

US 2020/0121937 A1 Apr. 23, 2020

Related U.S. Application Data

(63) Continuation of application No. 15/830,075, filed on Dec. 4, 2017, now Pat. No. 10,561,849, which is a (Continued)

(51) Int. Cl.
*A61N 1/372* (2006.01)
*G16H 40/67* (2018.01)
(Continued)

(52) U.S. Cl.
CPC ......... *G16H 40/67* (2018.01); *A61N 1/37217* (2013.01); *A61N 1/37254* (2017.08);
(Continued)

(58) Field of Classification Search
CPC ............ A61M 2205/3523; A61M 2205/3561; A61M 2205/52; A61M 5/14276;
(Continued)

(56) References Cited

U.S. PATENT DOCUMENTS 8,386,051 B2   2/2013 Rys
8,475,372 B2   7/2013 Schell et al.
(Continued)

OTHER PUBLICATIONS (PCT/US2017/013722) PCT Notification of Transmittal of the International Search Report and the Written Opinion of the International Searching Authority, dated Jun. 1, 2017, 11 pages.
(Continued)

*Primary Examiner* — George Manuel
(74) *Attorney, Agent, or Firm* — Shumaker & Sieffert, P.A.

(57) ABSTRACT

Systems, apparatus, methods and computer-readable storage media that facilitate monitoring the integrity of telemetry connectivity between an implantable device and an external device are provided. In one embodiment, an implantable device includes a monitoring component that monitors advertisement signal information identifying an amount of advertisement signals transmitted to the external device within a defined time period, and telemetry session information identifying an amount of the telemetry sessions that are established between the external device and the implantable device within the defined time period. A connectivity assessment component of the implantable device further determines whether a telemetry connectivity problem exists between the external device and the implantable device based on a degree of miscorrelation between the advertisement signal information and the telemetry session information.

20 Claims, 12 Drawing Sheets

Related U.S. Application Data continuation of application No. 15/011,161, filed on Jan. 29, 2016, now Pat. No. 9,833,628.

(51) Int. Cl.

| | |
|---|---|
| *A61N 1/05* | (2006.01) |
| *A61N 1/362* | (2006.01) |
| *A61N 1/36* | (2006.01) |
| *A61N 1/39* | (2006.01) |
| *A61N 1/365* | (2006.01) |
| *A61M 5/142* | (2006.01) |

(52) U.S. Cl.
CPC .......... *A61M 5/14276* (2013.01); *A61M 2205/3523* (2013.01); *A61M 2205/3561* (2013.01); *A61M 2205/52* (2013.01); *A61N 1/0563* (2013.01); *A61N 1/0568* (2013.01); *A61N 1/0573* (2013.01); *A61N 1/362* (2013.01); *A61N 1/3605* (2013.01); *A61N 1/36007* (2013.01); *A61N 1/36507* (2013.01); *A61N 1/36564* (2013.01); *A61N 1/3956* (2013.01)

(58) Field of Classification Search
CPC ............ A61N 1/0563; A61N 1/0568; A61N 1/0573; A61N 1/36007; A61N 1/3605; A61N 1/362; A61N 1/36507; A61N 1/36564; A61N 1/37217; A61N 1/37252; A61N 1/37254; A61N 1/3956; G16H 40/67

See application file for complete search history.

(56) References Cited

U.S. PATENT DOCUMENTS

| | | | |
|---|---|---|---|
| 9,008,917 B2 | 4/2015 | Gautama et al. | |
| 9,072,914 B2 | 7/2015 | Greenhut et al. | |
| 9,687,658 B2 | 6/2017 | Wu et al. | |
| 9,855,433 B2 | 1/2018 | Shahandeh et al. | |
| 2006/0161214 A1 | 7/2006 | Patel | |
| 2010/0121413 A1 | 5/2010 | Willerton et al. | |
| 2012/0172690 A1 | 7/2012 | Anderson et al. | |
| 2014/0113558 A1 | 4/2014 | Varoglu et al. | |
| 2014/0329465 A1 | 11/2014 | Palin et al. | |
| 2014/0330327 A1 | 11/2014 | Thompson-Nauman et al. | |
| 2015/0123810 A1 | 5/2015 | Hernandez-Rosas et al. | |
| 2015/0123812 A1* | 5/2015 | Hernandez-Rosas | A61B 5/076 340/870.02 |
| 2015/0133951 A1 | 5/2015 | Seifert et al. | |
| 2015/0148868 A1 | 5/2015 | Shahandeh et al. | |
| 2015/0341785 A1 | 11/2015 | Young et al. | |

OTHER PUBLICATIONS

European Search Report dated Sep. 3, 2020, corresponding to counterpart European Patent Application No. 20174206.; 6 pages.

* cited by examiner

| Advertisements Received | Monitored Telemetry Connectivity Information by External Device ||||||| 
|---|---|---|---|---|---|---|---|
| | Time | Type | Connection | RSSI | Average Throughput | Interrogation Sent | Interrogation Success |
| 1 | 10:12 | alert | yes | 46 dBm | 180 kbps | yes | yes |
| 2 | 11:32 | non-alert | no | 45 dBm | NA | NA | NA |
| 3 | 12:21 | non-alert | no | 47 dBm | NA | NA | NA |
| 4 | 13:01 | non-alert | no | 39 dBm | NA | NA | NA |
| 5 | 16:45 | alert | yes | 56 dBm | 179 kbps | yes | yes |
| 6 | 17:21 | non-alert | no | 44 dBm | NA | NA | NA |
| 7 | 19:33 | alert | no | 37 dBm | NA | NA | NA |
| 8 | 21:40 | non-alert | no | 38 dBm | NA | NA | NA |
| 9 | 22:50 | alert | yes | 47 dBm | NA | yes | no |
| 10 | 22:55 | non-alert | yes | 46 dBm | 128 kbps | NA | NA |

| Advertisements Received | Monitored Telemetry Connectivity Information by External Device | | | | | | |
|---|---|---|---|---|---|---|---|
| | Time | Type | Connection | Interrogation Received | RSSI | Interrogation Response Sent | Average Throughout |
| 1 | 10:12 | alert | yes | yes | 46 dBm | yes | 180 kbps |
| 2 | 10:35 | non-alert | no | NA | NA | NA | NA |
| 3 | 11:32 | non-alert | no | NA | NA | NA | NA |
| 4 | 12:00 | non-alert | no | NA | NA | NA | NA |
| 5 | 12:21 | non-alert | no | NA | NA | NA | NA |
| 6 | 12:54 | non-alert | no | NA | NA | NA | NA |
| 7 | 13:01 | non-alert | no | NA | NA | NA | NA |
| 8 | 15:36 | non-alert | no | NA | NA | NA | NA |
| 9 | 16:45 | alert | yes | yes | 56 dBm | yes | 179 kbps |
| 10 | 17:02 | non-alert | no | NA | NA | NA | NA |
| 11 | 17:21 | non-alert | no | NA | NA | NA | NA |
| 12 | 18:22 | non-alert | no | NA | NA | NA | NA |
| 13 | 19:33 | alert | no | NA | NA | NA | NA |
| 14 | 20:38 | non-alert | no | NA | NA | NA | NA |
| 15 | 21:40 | non-alert | no | NA | NA | NA | NA |
| 16 | 22:17 | non-alert | no | NA | NA | NA | NA |
| 17 | 22:30 | alert | yes | yes | 30 dBm | no | NA |
| 18 | 22:46 | non-alert | no | NA | NA | NA | NA |
| 19 | 22:55 | non-alert | yes | NA | 46 dBm | no | 128 kbps |
| 20 | 23:05 | non-alert | no | NA | 44 dBm | NA | NA |

FIG. 5

FACILITATING INTEGRITY OF TELEMETRY CONNECTIVITY BETWEEN A MEDICAL DEVICE AND A REMOTE DEVICE

This application is a continuation of U.S. patent application Ser. No. 15/830,075, (published as U.S. Publication No. 2018/0085592), filed Dec. 4, 2017 which was a continuation of U.S. patent application Ser. No. 15/011,161, filed Jan. 29, 2016, granted as U.S. Pat. No. 9,833,628, the content of both of which are incorporated herein by reference in their entirety.

TECHNICAL FIELD

This disclosure relates generally to implantable devices and, more particularly, to systems, apparatus, methods and computer-readable storage media facilitating integrity of telemetry connectivity between an implantable device and a remote device.

BACKGROUND

Modern healthcare facilitates the ability for patients to lead healthy and full lives. Implantable medical devices (IMDs) are often utilized for such medical advances. For example, IMDs such as pacemakers, implantable cardioverter-defibrillators (ICDs), neurostimulators, and drug pumps can facilitate management with a wide range of ailments, including, but not limited to, cardiac arrhythmias, diabetes, and Parkinson's disease. Modern IMDs are entrusted with vital tasks such as measuring and collecting data about vital signs and facilitating the provisioning of the collected data to doctors and nurses using telemetry communication. For example, in many applications, vital information is regularly and automatically communicated between an implantable device and a remote device, such as a remote device accessible to the patient wearing the implantable device and/or medical caregiver. Therefore, the integrity of telemetry connectivity between the implantable device and the remote device is of importance.

SUMMARY

The following presents a simplified summary of one or more of the embodiments including, but not limited to, provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include apparatus, methods and computer-readable storage media that facilitate monitoring the integrity of telemetry connectivity between an implantable device and an external device. In some embodiments, the implantable device is or includes an IMD. In other embodiments, the implantable device is or includes a device configured to interact with the IMD. In these embodiments, both the implantable device and the IMD can be implanted within a patient.

In one embodiment, an implantable device is provided. The implantable device can include: a memory that stores executable components; and a processor coupled to the memory and configured to execute the executable components stored in the memory. The executable components can include a monitoring component configured to monitor advertisement signal information identifying an amount of advertisement signals transmitted from the implantable device to the external device within a defined time period, and telemetry session information identifying an amount of telemetry sessions that are established between the external device and the implantable device within the defined time period. In addition, the implantable device can include a connectivity assessment component configured to determine whether a telemetry connectivity problem exists between the external device and the implantable device based on at least one of a number of discovery events within the defined time period or a ratio corresponding to the amount of telemetry sessions that are established between the external device and the implantable device within the defined time period relative to the amount of the advertisement signals transmitted to the external device within the defined time period.

In one embodiment, the connectivity assessment component is configured to determine that the telemetry connectivity problem exists between the external device and the implantable device based on at least one of the number of discovery events being less than a threshold number or the ratio being less than a threshold ratio.

The components of the implantable device can also include a notification component configured to generate a notification indicating the telemetry connectivity problem exists between the external device and the implantable device based on a determination that at least one of the number is below the threshold number or the ratio is below the threshold ratio. The notification component can also send the notification to the external device for rendering at the external device or for relaying, by the external device, to another device.

In another embodiment, the implantable device can include a configuration component configured to receive a command instructing the implantable device to reconfigure a telemetry communication protocol employed by the implantable device to communicate with the external device based on a determination that an amount of the advertisement signals that are received by the external device from the implantable device within the defined time period is below a threshold amount.

In another embodiment, a method is provided. The method can include monitoring, by a device including a processor, telemetry connectivity information including advertisement signal information identifying times advertisement signals are received by the device from an implantable device. The method can also include determining, by the device, whether a telemetry connectivity error condition exists associated with performing telemetry communication between the device and the implantable device based on an amount of the advertisement signals received within a defined time period relative to a threshold amount. The method can also include, generating, by the device, a notification identifying the telemetry connectivity error condition based on a determination that the telemetry connectivity error condition exists.

In one embodiment, the determining that the telemetry connectivity error condition exists is based on the amount of the advertisement signals received within the defined time period being below the threshold amount. In some embodiments, the method also includes performing at least one of rendering, by the device, the notification at the device, or transmitting, by the device, the notification to another device, wherein the other device includes the implantable device or a server device.

In one embodiment, the determining also includes determining that the telemetry connectivity error condition exists based on a duration of time between reception of two or more of the advertisement signals being above a threshold duration.

In some embodiments, the telemetry connectivity information also includes telemetry session information identifying an amount of telemetry sessions established between the device and the implantable device within the defined time period. The determining whether the telemetry connectivity error condition exists can be also based on a percentage value corresponding to the amount of telemetry sessions established relative to the amount of the advertisement signals received being less than a threshold percentage value.

In yet another embodiment, a system is provided. The system can include an implantable device configured to transmit advertisement signals using a defined telemetry communication protocol. The system can also include an external device configured to perform telemetry communication with the implantable device based on reception of the advertisement signals, and monitor advertisement signal information identifying an amount of the advertisement signals received by the external device within a defined period of time. The external device can further facilitate determining whether a telemetry connectivity error condition exists in association with performance of the telemetry communication with the implantable device based on evaluation of the advertisement signal information with respect to the defined telemetry communication protocol. In various embodiments, the system can further include a server device, wherein the external device is configured to send the advertisement signal information to the server device and the server device is configured to perform the evaluation. For example, the server device can determine that the telemetry connectivity error condition exists based on a determination that the amount of the advertisement signals received is below a threshold amount.

In yet another embodiment, a device configured to communicate with an implantable device is provided. The device can include: a memory that stores executable components; and a processor coupled to the memory and configured to execute the executable components stored in the memory. The executable components can include a communication component configured to facilitate performance of telemetry communication between the device and an implantable device, and a monitoring component configured to monitor telemetry connectivity information including advertisement signal information identifying times at which advertisement signals, transmitted by the implantable device, are received by the device. The device can further include a connectivity assessment component configured to determine whether a telemetry connectivity error condition exists associated with the performance of telemetry communication with the implantable device based on an amount of the advertisement signals received within a defined time period relative to a threshold amount. The communication component can facilitate the performance of telemetry communication between the device and the implantable device using a BLUETOOTH® Low Energy communication protocol.

In some embodiments, a notification component of the device is configured to generate a notification identifying the telemetry connectivity error condition based on a determination that the telemetry connectivity error condition exists. The communication component of the device can further be configured to transmit the notification to another device, such as the implantable device or a server device. In one embodiment, the telemetry connectivity information further include telemetry session information identifying an amount of telemetry sessions established between the device and the implantable device within the defined time period. According to this implementation, the connectivity assessment component is further configured to determine that the telemetry connectivity error condition exists based on a percentage value representative of the amount of advertisement signals received relative to the amount of the telemetry sessions established being less than a threshold percentage value.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

BRIEF DESCRIPTION OF THE DRAWINGS

FIG. 3 illustrates a block diagram of an example, non-limiting table including telemetry connectivity information monitored by an external device in accordance with one or more embodiments described herein.

FIG. 5 illustrates a block diagram of an example, non-limiting table including telemetry connectivity information monitored by an implantable device in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth including, but not limited to, provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures can depict example arrangements of components, additional and/or intervening components can be present in one or more embodiments.

Figure 1:
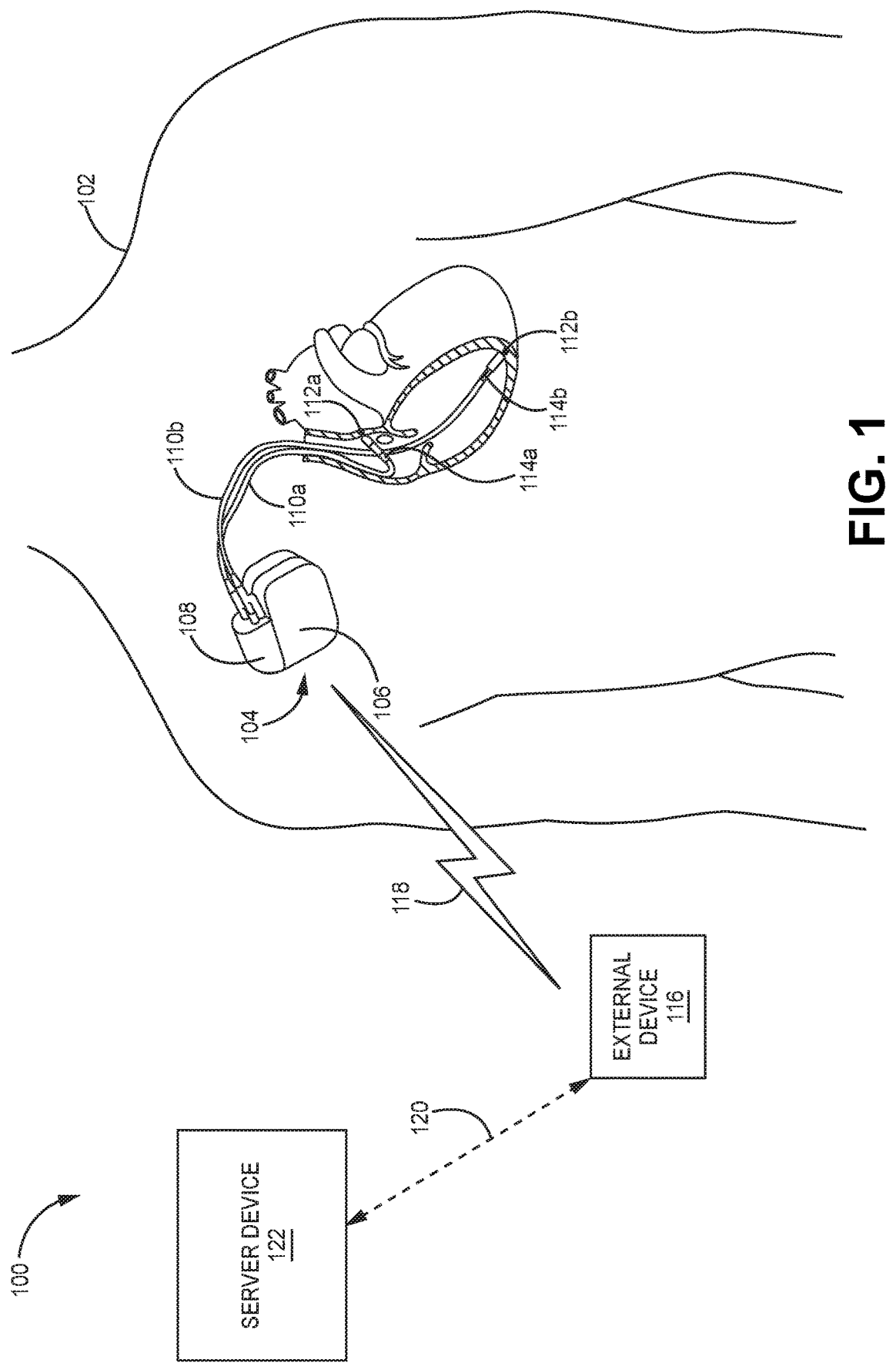
FIG. 1 illustrates a schematic diagram of an example, non-limiting medical device telemetry system that monitors integrity of telemetry connectivity between an implantable device and an external device in accordance with one or more embodiments described herein.

With reference now to the drawings, FIG. 1 illustrates a schematic diagram of an example, non-limiting, medical device telemetry system 100 for monitoring integrity of telemetry connectivity between an implantable device and an external device in accordance with one or more embodiments described herein. In the embodiment shown, medical device telemetry system 100 includes an implantable device 104 implanted within a body 102, an external device 116, and a server device 122. While the server device 122 is shown in FIG. 1, in some embodiments, the medical device telemetry system 100 includes the implantable device 104 and the external device 116 but need not include the server device 122.

In some embodiments, the implantable device 104 is an IMD that is also configured to facilitate one or more diagnostic or treatment functions relative to the body 102. In other embodiments, the implantable device 104 is separate from an IMD (not shown in this embodiment) that is also implanted within the body 102 and communicatively and/or electrically coupled to the IMD.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

Various embodiments of medical device telemetry system 100 are described in connection with operations including monitoring the integrity of telemetry connectivity between the implantable device 104 and the external device 116. The implantable device 104 and the external device 116 are configured to use telemetry communication link 118 to exchange various types of information. In some embodiments, the implantable device 104 and the external device 116 can establish a trusted wireless personal area network (PAN) via the telemetry communication link 118. After establishing the PAN, the external device 116 and the implantable device 104 can communicate information. For example, using the telemetry communication link 118, the external device 116 can read data captured by the implantable device 104 (e.g., physiological or biometric data, such as electrogram data, performance data regarding operation of the implantable device 104, etc.).

In another example, using the telemetry communication link 118, the external device 116 can send programming/configuration information to the implantable device 104 for application by the implantable device 104. The implantable device 104 can also transmit, using the telemetry communication link 118, information to the external device 116. The information can include, but is not limited to, sensed physiological data, diagnostic determinations made based on the sensed physiological data, and/or performance data regarding operation of the implantable device 104 (e.g., remaining batter level, logged information regarding timing of reception/transmission of signals, received signal strength indicator (RSSI) information, throughput of received data packets, number of successfully completed telemetry sessions, etc.).

In some embodiments, the external device 116 can also provide information received from the implantable device 104 (and/or determinations or inferences made at the external device 116 based on the information) to a server device 122 via another communication link 120. For example, communication link 120 can include a telemetry communication link established between the external device 116 and the server device 122 using a wide area network (WAN). By way of example, but not limitation, the server device 122 can be associated with a networked medical monitoring service that is configured to remotely monitor information collected by implantable devices worn by patients (e.g., implantable device 104). The server device 122 can monitor and log the data, process the data and/or provide other users (e.g., medical caregiver personnel) access to the data via a telecommunication network.

In some embodiments, the server device 122 can also notify one or more user devices in response to reception of information that indicates a trigger event. For example, the server device 122 can notify a patient device (e.g., a device associated with the person wearing the implantable device 104) and/or the caregiver device in response to reception of physiological information indicating the patient's heart electrical activity is abnormal. In another example, the server device 122 can notify a patient device and/or the caregiver device in response to reception of information indicating telemetry connectivity between the implantable device 104 and the external device 116 is or may be compromised.

The external device 116, the implantable device 104, and/or the server device 122 can communicate using various wireless communication protocols configured to facilitate telemetry communication between devices over various distances. For example, the respective devices can communicate with one another using communication protocols including, but not limited to, a near field communication (NFC) based protocol, a BLUETOOTH® technology-based protocol (e.g., BLUETOOTH® low energy (BLE) protocol), a ZigBee® protocol, a WirelessHART® protocol, a Z-Wave® based communication protocol, an advanced and adaptive network topology (ANT) based protocol, a radio frequency (RF) based communication protocol, an Internet Protocol (IP) based communication protocol (e.g. hyper text transfer protocol (HTTP), session initiation programming (SIP), IP version 6 over low power wireless personal area networks (6LoWPAN), etc.), a cellular communication protocol, an ultra-wideband (UWB) technology-based protocol, or other forms of communication, including both proprietary and non-proprietary communication protocols.

In various embodiments, communication between the respective devices of medical device telemetry system 100

(e.g., implantable device 104, external device 116, and server device 122) can be facilitated over a personal area network (PAN) or a local area network (LAN) (e.g., a Wireless Fidelity (Wi-Fi) network) that can provide for communication over greater distances than the NFC or BLE protocol and can provide other advantages (e.g., stronger encryption protocols). In other embodiments, the external device 116, the implantable device 104 and/or the server device 122 can communicate with one another and/or another device (e.g., another server device or a second external device) over a wide area network (WAN) using HTTP-based communication protocols. In one embodiment, the external device 116 is configured to communicate with the implantable device 104 and the server device 122 using disparate communication protocols and/or disparate communication networks. For example, the external device 116 and the implantable device 104 can establish a PAN and communicate using BLE and the external device 116 and the server device 122 can be connected via a LAN or a WAN and communicate using a cellular or IP based communication protocol. In other embodiments, the respective devices of medical device telemetry system 100 can be configured to communicate using same or similar communication protocols via same or similar telecommunication networks.

The external device 116 can include a wide variety of computing devices. For example, the external device 116 can include, but is not limited to, a personal computing (PC) device, such as a smartphone, a tablet PC, a notebook, a personal digital assistant (PDA), a wearable device, or another type of handheld computing device. In some embodiments, the external device 116 includes a PC that is associated with the user wearing the implantable device 104. For example, the external device 116 can include a smartphone or other type of handheld or wearable device that is owned and operated by the patient wearing the implantable device 104. In another example, the external device 116 can include a PC that is operated by a medical caregiver of the patient, such as the patient's physician, nurse, at-home caregiver, mother, etc. In yet another example, the external device 116 can include a dedicated and/or stationary electronic computing device designed to remain at a home of the patient or at an office of a physician.

In various exemplary embodiments, the external device 116 includes an off-the-shelf device purchased at a store that can be configured to perform a variety of computing applications. These devices are configured to employ various types of commercially available telemetry protocols to communicate with other devices. For example, many modern mobile devices such as smartphones, tablet personal computer (PC), and the like are configured to communicate using public telemetry protocols, including, but not limited to, BLUETOOTH® based communication protocols (e.g., BLE), NFC, Wi-Fi, Zigbee®, RF4CE, WirelessHART, 6LoWPAN, Z-Wave, ANT, and the like. The use of such commercially available telemetry protocols for wireless communication between implantable devices (e.g., implantable device 104) and external devices (e.g., external device 116) more easily facilitates widespread provisioning of telemetry solutions.

Medical device telemetry system 100 provides various techniques for monitoring the integrity and quality of telemetry connectivity between the implantable device 104 and the external device 116. Medical device telemetry system 100 also provides techniques for diagnosing telemetry connectivity problems detected between the implantable device 104 and the external device 116. For example, medical device telemetry system 100 can identify when the telemetry communication link 118 between the external device 116 and the implantable device 104 fails to facilitate exchange or efficiently exchange information between the external device 116 and the implantable device 104 in accordance with a defined telemetry communication scheme employed by the respective devices.

In response to a determination that a telemetry connectivity problem between the external device 116 and the implantable device 104 exists, medical device telemetry system 100 can also provide a notification regarding the telemetry connectivity problem. For example, the notification can be provided to the patient wearing the implantable device 104, a medical caregiver associated with the patient wearing the implantable device, a user operating the external device 116, a system associated with monitoring information detected by the implantable device 104, etc.

The techniques employed by medical device telemetry system 100 to monitor and evaluate the integrity and quality of wireless telemetry connectivity between the external device 116 and the implantable device 104 can be applied to various types of wireless telemetry communication protocols. In one or more exemplary embodiments, these techniques are tailored to monitor and evaluate the integrity and quality of wireless telemetry connectivity between the implantable device 104 and the external device 116 facilitated using commercially available (e.g., open access) short range wireless telemetry communication protocol, such as BLE communication protocol and the like.

In one or more embodiments, the external device 116, the implantable device 104, and/or the server device 122 are configured to monitor telemetry connectivity information associated with performance of telemetry communication between the external device 116 and the implantable device 104. For example, the external device 116 can log signal information associated with signals received by the external device 116 from the implantable device 104 and/or signals transmitted by the external device 116 to the implantable device 104. The signal information can include, but is not limited to, timing of reception of advertisement or beacon signals transmitted by the implantable device 104, occurrence of successful connection events between the external device 116 and the implantable device 104, RSSI information associated with strengths of signals received from the implantable device 104, timing of interrogation signals sent by the external device 116 to the implantable device 104, number of the interrogation signals to which the implantable device 104 successfully responded, throughput of data packets received from the implantable device 104 (e.g., downlink throughput), and throughput of data packets transmitted to the implantable device 104 (e.g., uplink throughput).

Similarly, the implantable device 104 can log signal information associated with signals received from the external device 116 and signals transmitted by the implantable device 104 to the external device 116. For example, the implantable device 104 can log signal information including, but not limited to, timing of advertisement or beacon signals sent by the implantable device 104, occurrence of successful connection events between the external device 116 and the implantable device 104, RSSI information associated with strengths of signals received from the external device 116, timing of interrogation signals received from the external device 116, timing of interrogation response data packets sent by the implantable device 104, throughput of data packets received from the external device 116, and throughput of data packet transmitted to the external device 116.

In various embodiments, telemetry connectivity information monitored by the external device 116 and/or the implantable device 104 can be provided to the server device 122 for evaluation by the server device to identify and diagnose connectivity problems between the implantable device 104 and the external device 116. For example, the external device 116 can forward external device logged signal information to the server device 122 via communication link 120. When the telemetry communication link 118 between the external device 116 and the implantable device 104 is established and operational, the implantable device 104 can send the external device 116 logged implantable device signal information via telemetry communication link 118. The external device 116 can also forward such information to the server device 122.

One or more of the respective devices of medical device telemetry system 100 (e.g., the external device 116, the implantable device 104 and/or the server device 122) can further process the monitored telemetry connectivity information to determine whether a connectivity problem exists between the external device 116 and the implantable device 104. The phrase "telemetry connectivity problem" is used broadly herein to refer to the occurrence of a connectivity error condition associated with telemetry communication between the implantable device 104 and the external device 116 that is marked by an inability or hindered ability for the implantable device 104 to communicate with the external device 116, and vice versa, according to a defined telemetry communication scheme employed by the respective devices.

For example, a telemetry connectivity error condition can include an inability for the external device 116 and the implantable device 104 to connect altogether (e.g., establish a telemetry communication link 118). In another example, a telemetry connectivity error condition can include an inability for the implantable device 104 and the external device 116 to maintain telemetry communication link 118. In another example, a telemetry connectivity error condition can include data throughput below a defined value or meeting a defined condition. In another example, a telemetry connectivity error condition can include inconsistent data throughput associated with data communicated between the external device 116 and the implantable device 104 after establishing the telemetry communication link 118. Inconsistent data throughput can include, but is not limited to, the occurrence of throughput values varying a defined amount over a defined amount of time.

In another example, a telemetry connectivity error condition can include a decryption error or formatting error associated with data packets that are received by the external device 116 from the implantable device 104, and vice versa. In yet another example, a telemetry connectivity error condition can include an inability for the external device 116 and/or the implantable device 104 to communicate defined information between one another according to a defined communication schedule.

Telemetry connectivity error conditions associated with telemetry communication between the external device 116 and the implantable device 104 can be attributed to various causes including, but not limited to, usage of incompatible telemetry communication protocol by the respective devices, usage of outdated telemetry communication protocols by one or both of the devices, an error associated with configuration of the telemetry communication protocol employed by the one or both of the devices, a hardware malfunction associated with one or both of the devices, interference associated with a communication channel employed by the respective devices to communicate, and/or separation of the devices beyond the maximum distance via which the telemetry communication protocol employed by the devices can facilitate communication.

Another possible cause of telemetry connectivity issues between the external device 116 and the implantable device 104 could be related to the location of the implantable device 104 within the body 102. For example, when the implantable device 104 is implanted within the body about 4.0 or more centimeters beneath the skin, the implantable device 104 is considered a "deep implant." Some deep implants may experience connectivity issues with certain external devices based in part on interference associated with internal body structures around or near the deep implant.

Yet another possible cause of telemetry connectivity issues between the external device 116 and the implantable device 104 can be attributed to a telemetry shut down or time-out protocol employed by the implantable device 104. For example, in some implementations, the implantable device 104 can be configured to temporarily deactivate telemetry to conserve battery power upon the occurrence of various triggers detected by the implantable device 104 (e.g., reception of a threshold amount of telemetry requests from devices that are unauthorized to communicate with the implantable device 104). In this scenario, a detected connectivity issue in which the external device 116 is unable to connect with the implantable device 104 would be intentional. Nevertheless, the external device 116 and the implantable device can differentiate between intentional and unintentional connectivity issues.

The respective devices of medical device telemetry system 100 (e.g., the external device 116, the implantable device 104, and the server device 122) can employ various techniques to identify the occurrence of telemetry connectivity error condition associated with performance of telemetry communication between the external device 116 and the implantable device 104. For example, the external device 116, the implantable device 104 and/or the server device 122 can compare monitored telemetry connectivity information against previously determined parameters for telemetry connectivity reference information associated with proper telemetry connectivity and/or telemetry connectivity reference information for improper telemetry connectivity. The results of the comparison can be employed to determine whether a connectivity error condition exists between the implantable device 104 and the external device 116.

In particular, in various embodiments, the external device 116 and the implantable device 104 are configured to utilize a defined telemetry communication protocol (e.g., BLE) that instructs the external device 116 and the implantable device 104 how to communicate with other devices. For example, the external device 116 and the implantable device 104 can be configured to initially operate in a discovery mode wherein the external device 116 and the implantable device 104 perform telemetry communication operations that allow the external device 116 and the implantable device 104 to discover each other. In some embodiments, prior to communicating a defined type of information with each other (e.g., data packets that include trusted information), and/or prior to communicating using a defined communication radio frequency, after discovery, the implantable device 104 and the external device 116 can be configured to perform an authentication process wherein the respective devices determine whether they are authorized to establish a secure telemetry connectivity link (e.g., telemetry communication link 118) with one another. In some implementations, the implantable device 104 and the external device 116 can be configured to pair with one another in association with performing the authentication process. For example, the implantable device 104 and the external device 116 can form a trusted relationship wherein the implantable device 104 can communicate with the external device 116, and vice versa, after discovery, authentication and pairing is established, without performing additional discovery and authentication processes. After the implantable device 104 and the external device 116 discover each other, pair, and/or perform authentication, they can continue to communicate with each other according to the defined communication protocol.

The parameters of the defined communication protocol can be agreed upon between the devices in association with discovery, pairing and/or authentication and/or can be configured or stored in memory of the respective devices. The parameters of the communication protocol can also vary depending on the one or more applications being executed by the respective devices. For example, the parameters of the communication protocol can define what type of data the respective devices are to communicate with one another and how the data should be formatted. The parameters of the communication protocol can also define how the devices are to communicate different types of data with one another (e.g., using one-way communications or two-way communications, duration between communication signals, number of data packets transmitted, receiver and transmitter activation and deactivation periods, etc.), and when the devices are to communicate different types data with one another. The parameters of the communication protocol can also define one or more desired RSSI values for signals communicated between the respective devices, and one or more desired throughput values for data packets communicated between the respective devices.

In various embodiments, the external device 116, the implantable device 104, and/or the server device 122 can evaluate monitored telemetry connectivity information (e.g., signal information logged by the external device 116 and/or the implantable device 104) based on the defined communication protocol parameters to determine whether a telemetry connectivity error condition exists between the implantable device 104 and the external device 116. For example, the external device 116, the implantable device 104, and/or the server device 122 can compare the logged signal information regarding timing of receipt of certain signals, timing of transmission of certain signals, RSSI values associated with received signals, throughput of received data packets, etc. with reference signal information for the defined communication protocol parameters that identify when the certain signals should be received and/or transmitted, what RSSI levels should be associated with the received signals and what throughput values should be associated with received data packets. Based on the comparison, the external device 116, the implantable device 104 and/or the server device 122 can determine whether and to what degree aspects of the logged signal information deviates or agrees with the defined communication protocol. For example, the respective devices can determine that a telemetry connectivity error condition associated with performance of telemetry communication between the implantable device 104 and the external device 116 exists based on a determination that one or more aspects of the logged signal information deviates (e.g., with respect to a threshold value or threshold range) from the defined communication protocol parameters.

In some embodiments, the external device 116 and the implantable device 104 can further diagnose a cause of an identified telemetry connectivity error condition and/or determine one or more steps to correct the error condition based on evaluation of the monitored telemetry connectivity information. For example, the external device 116 and the implantable device 104 can determine whether the telemetry connectivity error condition is associated with a particular hardware failure, a particular configuration problem, or channel interference.

In one embodiment, the implantable device 104 is configured to evaluate the integrity and/or performance quality of telemetry communication between the external device 116 and the implantable device 104 based on reception, by the external device 116, of advertisement signals transmitted by the implantable device 104. As used herein, advertisement signals can also include beacon signals. Reception of an advertisement signal by the external device 116 from the implantable device 104 is referred to herein as a discovery event.

For example, in accordance with various short range communication protocols that can be employed for telemetry communication between two devices (e.g., BLE communication protocol), a second device can be configured to conduct a telemetry communication session with a first device after receiving an advertisement signal from the first device.

In accordance with this embodiment, the implantable device 104 is configured to transmit advertisement signals to facilitate establishing a telemetry communication session with the external device 116. For example, the advertisement signals can indicate the implantable device 104 is ready and available to communicate with the external device 116. The external device 116 is configured to establish a telemetry communication session with the implantable device 104 based on reception of an advertisement signal. The number, frequency and/or timing of advertisement signals to be transmitted by the implantable device 104 can be defined based on the defined telemetry communication protocol employed by implantable device 104 and the external device 116. For example, the implantable device 104 can be configured to transmit N (e.g., 480) advertisement signals within an X hour period (e.g., 24 hour period). In some embodiments, one advertisement signal can be transmitted approximately every three minutes. In another example, the implantable device 104 can be configured to transmit advertisement signals at a frequency of M (e.g., 20) advertisement signals every Y minutes (e.g., 60 minutes). In another example, the implantable device 104 can be configured to transmit one advertisement signal every K seconds (e.g., 60 seconds).

In other embodiments, the implantable device 104 can transmit advertisement signals according to a defined schedule or based on occurrence of trigger events. For example, the implantable device 104 can transmit M signals at a K frequency between the hours of 10 am and 6 pm and transmit N signals at an L frequency between the hours of 6 pm and 10 am. In another example, the implantable device 104 can transmit advertisement signals at an increased frequency based on detection of information by the implantable device 104 (e.g., biometric information) indicative of a trigger event (e.g., the biometric information is outside a specified range). It should be appreciated that numerical values for the communication parameters represented by variables N, X, M, Y, K, L, etc. can change from time to time.

According to this embodiment, the external device 116 can monitor or log advertisement signal information identifying reception of advertisement signals from the implantable device 104. For example, the external device 116 can monitor or log information identifying a number of advertisement signals received over a defined period of time (e.g., 24 hours). The external device 116 can also time-stamp one or more (or, in some embodiments, each) advertisement signals received. The external device 116 can thus track a frequency of received advertisement signals over a defined time period or window of time and monitor duration between received advertisement signals. The external device 116 can be configured to perform such monitoring or tracking of advertisement signal information on a continual basis. For example, the external device 116 can be configured to log advertisement signal information for consecutive periods of time (e.g., every day) or according to a defined schedule (e.g., every other day).

In one embodiment, the external device 116 is further configured to evaluate the logged advertisement signal information to identify telemetry connectivity error conditions associated with performance of telemetry communication between the implantable device 104 and the external device 116. In addition, or as an alternative, to performing the evaluation, the external device 116 can forward the logged advertisement signal information to the implantable device 104 and/or the server device 122 for evaluation. The external device 116, the implantable device 104 and/or the server device 122 can evaluate the logged advertisement signal information based on defined telemetry communication protocol parameters (e.g., defined in memory of the respective devices or otherwise accessible to the respective devices, for example, over a network) that relate an amount, a timing and/or a frequency of advertisement signals received by the external device to one or more telemetry connectivity error conditions.

For example, the respective devices can determine that a connectivity error condition associated with performance of telemetry communication between the implantable device 104 and the external device 116 exists based on a number of received advertisement signals within a defined period of time being below a threshold number.

In another example, the respective devices can identify the occurrence of a telemetry connectivity error condition associated with performance of telemetry communication between the implantable device 104 and the external device 116 based on a number of received advertisement signals within the defined period of time being above a particular threshold number. In another example, the respective devices can identify the occurrence of a telemetry connectivity error condition associated with performance of telemetry communication between the implantable device 104 and the external device 116 based on a frequency of received advertisement signals within the defined window of time being above or below a threshold frequency value or range.

In another example, the respective devices can identify the occurrence of a telemetry connectivity error condition associated with performance of telemetry communication between the implantable device 104 and the external device 116 based on a duration between received advertisement signals being above or below a defined threshold duration. Still in another example, the respective devices can identify the occurrence of a telemetry connectivity error condition associated with performance of telemetry communication between the implantable device 104 and the external device 116 based on reception of advertisement signals not according to a defined schedule or not in accordance with a specific operation mode associated with occurrence of a trigger event (e.g., the frequency of advertisement signals received did not increase following reception of information from the implantable device identifying the trigger event).

In response to a determination that a telemetry connectivity problem between the external device 116 and the implantable device 104 exists, the respective devices of medical device telemetry system 100 (e.g., the external device 116, the implantable device 104 and/or the server device 122) can further provide a notification (e.g., to the patient wearing the implantable device 104, to a user operating the external device 116, to a medical caregiver, to a system responsible for monitoring information, etc.) regarding the telemetry connectivity error condition. For example, in one embodiment, in response to a determination made by the external device 116 that a telemetry connectivity error condition associated with telemetry communication between the external device 116 and the implantable device 104 exists, the external device 116 can generate and render a notification at the external device 116. For example, the notification can include a visual notification, such as a flashing light activated at the external device 116, and/or text or image data displayed at the external device 116 (e.g., via a display screen) that identifies the telemetry connectivity problem. In another example, the notification can include an audible alarm.

In another implementation, in response to a determination made by the external device 116 that a telemetry connectivity problem exists between the external device 116 and the implantable device, the external device 116 can generate a notification regarding the connectivity problem and send the notification to another device, such as the server device 122 and/or send the notification to another device (not shown) associated with a physician, caregiver, family member and/or friend of the patient wearing the implantable device 104.

In another implementation, in response to a determination made by the server device 122 that a telemetry connectivity problem between the external device 116 and the implantable device 104 exists, the server device 122 can generate a notification regarding the connectivity problem and send the notification to the external device 116 for rendering at the external device 116. In other implementations, the server device 122 can send the notification to another device (not shown) associated with a physician, caregiver, family member and/or friend of the patient wearing the implantable device 104. In yet another implementation, in response to a determination made by the implantable device 104 that a connectivity problem exists, the implantable device 104 can generate and send a notification to the external device 116 for rendering at the external device 116 and/or for forwarding, by the external device 116, to the server device 122 and/or another device (not shown) associated with a physician, caregiver, family member and/or friend of the patient wearing the implantable device 104. Additional aspects and embodiments of the subject telemetry connectivity integrity monitoring and evaluation techniques are discussed infra with respect to FIGS. 2-11.

It is to be appreciated that the implantable device 104 and the external device 116 can include one or more devices, transducers and/or circuits that can facilitate telemetry communication and telemetry integrity communication monitoring and evaluation. For example, the implantable device 104 and the external device 116 can respectively include a transmitter or transceiver that transforms electrical power into a signal associated with transmitted data packets. Additionally, the implantable device 104 and the external device 116 can include one or more devices, transducers, receivers and/or circuits that can facilitate receiving information from one or more devices. For example, the implantable device 104 and the external device can respectively include a receiver that transforms a signal into electrical power.

In the example shown in medical device telemetry system 100, a person operating the external device 116 is a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of implantable devices configured to communicate with the external device 116 or another external device. The particular, size, shape, placement and/or function of the implantable device 104 is not critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110a,b connected to the housing 106. The leads 110a,b extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. When implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b can be formed to define fixation mechanisms of other structures. In other instances, leads 110a,b can include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 can include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors can electrically couple to circuitry, such as therapy circuitry or sensing circuitry, of the implantable device 104 via connections in connector block 108.

In one or more embodiments, the implantable device 104 is configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory. Implantable device 104 can also receive sensed electrical signals on the electrical conductors from one or more of electrodes 112a and 112b and 114a and 114b. The implantable device 104 can sense the electrical signals using either a unipolar or bipolar electrode configuration. Sensing circuitry of the implantable device 104 may process the sensed electrical signals and the implantable device 104 may analyze the processed and/or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead can be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 can include no leads, as in the case of an intracardiac pacemaker or a leadless pressure sensor. In the case of an intracardiac pacemaker, the device can include a housing sized to fit wholly within the patient's heart. In one example, the housing can have a volume that is less than 1.5 cc and, more preferably, less than 1.0 cubic centimeter (cc). However, the housing can be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

Figure 2:
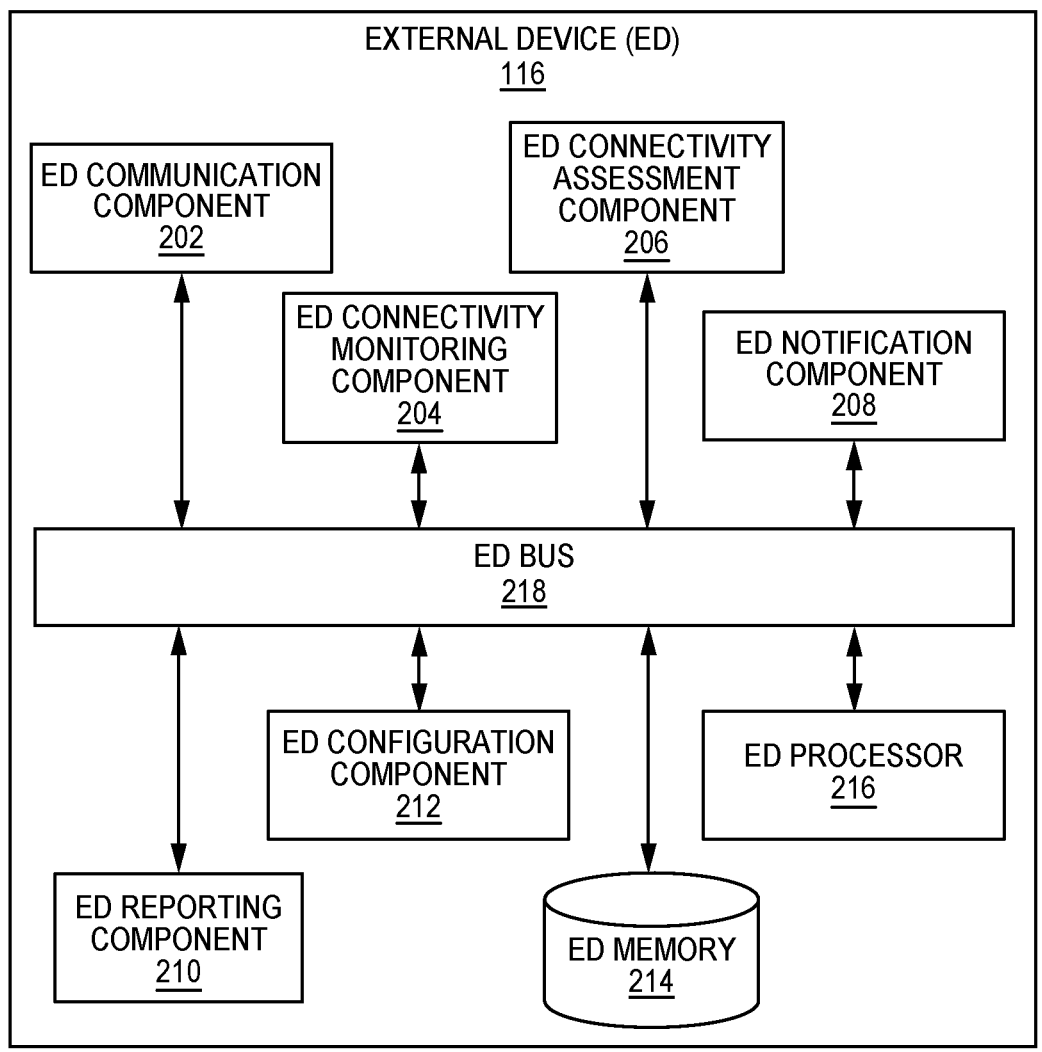
FIG. 2 illustrates a block diagram of an example, non-limiting external device for which integrity of telemetry connectivity with an implantable device is monitored in accordance with one or more embodiments described herein.

Referring now to FIG. 2, illustrated is a block diagram of an example, non-limiting, external device 116 in accordance with one or more embodiments described herein. The external device 116 includes an external device (ED) communication component 202, an ED connectivity monitoring component 204, an ED connectivity assessment component 206, an ED notification component 208, an ED reporting component 210, and an ED configuration component 212.

One or more of the components of external device 116 constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The external device 116 can include ED memory 214 for storing the computer executable components and instructions, and ED processor 216 to facilitate operation of the computer executable components and instructions by external device 116. The external device 116 can include an ED bus 218 that couples the various components of the external device 116, including, but not limited to, the ED communication component 202, the ED connectivity monitoring component 204, the ED connectivity assessment component 206, the ED notification component 208, the ED reporting component 210, the ED configuration component 212, the ED processor 216 and/or the ED memory 214. Repetitive description of like elements employed in other embodiments described herein is omitted for sake of brevity.

With reference to FIGS. 1 and 2, the external device 116 can include any suitable computing device configured to communicate with the implantable device 104, and in some implementations, the implantable device 104 and the server device 122. For example, the external device 116 can include, but is not limited to, a handheld computing device, a mobile phone, a smart phone, a tablet PC, a laptop computer, a desktop computer, a personal digital assistant (PDA) and/or a wearable device. In some embodiments, the external device 116 can include a display that can present information associated with the implantable device 104. In another embodiment, the external device 116 can include an application and/or a program associated with the implantable device 104.

The ED communication component 202 is configured to facilitate telemetry communication between external device 116 and the implantable device 104. For example, the ED communication component 202 can include or be various hardware and software devices associated with establishing and/or conducting a telemetry communication between the external device 116 and implantable device 104. For example, ED communication component 202 can control operation of a transmitter-receiver or transceiver (not shown) of the external device 116 to establish a telemetry session with the implantable device 104 and to control transmission and reception of signals or data packets between the external device 116 and the implantable device 104.

The ED communication component 202 can facilitate telemetry communication between the external device 116 and the implantable device 104 using a variety of telemetry communication protocols. For example, the ED communication component 202 can communicate with the implantable device 104 using communication protocols including, but not limited to, a NFC based protocol, a BLUETOOTH® technology-based protocol, a ZigBee® based protocol, a WirelessHART® based protocol, a Z-Wave® based protocol, an ANT based protocol, an RF based communication protocol, an IP based communication protocol, a cellular communication protocol, a UWB technology-based protocol, or other forms of communication including both proprietary and non-proprietary communication protocols.

In various embodiments, with reference to FIGS. 1 and 2, the ED communication component 202 is configured to control transmission and reception of information between the external device 116 and the implantable device 104 via a telemetry communication link (e.g., telemetry communication link 118) facilitated by a communication protocol utilizing lower energy consumption than a conventional communication protocol for wirelessly transmitting data. In a non-limiting example, the ED communication component 202 controls transmission and reception of data packets between the external device 116 and the implantable device 104 using BLE protocol. While the example provided describes communication according to the BLE protocol, other communication protocols can be employed.

In some embodiments, the ED communication component 202 is also configured to facilitate communication between the external device 116 and other devices, such as server device 122. For example, the ED communication component 202 can employ a same or similar telemetry communication protocol used to communicate with implantable device 104 to communicate with server device 122. In another implementation, the ED communication component 202 can employ a different communication protocol to communicate with the server device 122 relative to that used to communicate with the implantable device 104. For example, the ED communication component 202 can communicate with the implantable device 104 using a short-range wireless telemetry communication protocol (e.g., BLE and the like), and with the server device 122 using a wide-range wireless telemetry communication protocol (e.g., an IP or cellular based communication protocol). Still in other embodiments, the ED communication component 202 can communicate with the server device 122 via a wired connection.

ED connectivity monitoring component 204 is configured to monitor information associated with the integrity and quality of telemetry connectivity between the external device 116 and the implantable device 104, referred to herein as telemetry connectivity information. For example, after establishing an initial connection with the implantable device 104, pairing with the implantable device 104, or otherwise establishing an authorized telemetry communication link (e.g., a telemetry communication link 118) with the implantable device 104, the ED connectivity monitoring component 204 can monitor telemetry connectivity information over the course of operation of the implantable device 104. In another example, the ED connectivity monitoring component 204 can monitor telemetry connectivity information according to a temporal cycle or schedule. In yet another example, the ED connectivity monitoring component 204 can randomly monitor telemetry connectivity information. Still in yet another example, the ED connectivity monitoring component 204 can monitor telemetry connectivity information in response to a request command provided by the external device 116 (e.g., a request command based on user input at the external device 116 or a request command issued by the server device 122 and transmitted to the external device via communication link 120). According to this example, the request can be associated with a request to perform an assessment on the quality and integrity of telemetry connectivity between the implantable device 104 and the external device 116. The request can define a type of telemetry connectivity information for the external device 116 to monitor and period of time over which to monitor the telemetry connectivity information. The telemetry connectivity information monitored by the ED connectivity monitoring component 204 can be used by the external device 116, the implantable device 104 and/or the server device 122 to determine whether a telemetry connectivity error condition exists in association performing telemetry communication between the external device 116 and the implantable device.

In one embodiment, the external device 116 can log or store the telemetry connectivity information in ED memory 214. The ED connectivity monitoring component 204 can remove all or portions of the logged telemetry connectivity information over time for replacement with new telemetry connectivity information. In another implementation, in addition or in the alternative to storing the telemetry connectivity information, the external device 116 can send the monitored telemetry connectivity information to the implantable device 104 and/or the server device 122 via ED reporting component 210 and/or ED communication component 202. For example, the ED reporting component 210 and/or the ED communication component 202 can send monitored telemetry connectivity information to the server device 122 in real-time or substantially real-time as the telemetry connectivity information is monitored. As used herein, the term "real-time" means within a defined number of nanoseconds or milliseconds. According to this implementation, the ED reporting component 210 can send the monitored telemetry connectivity information to the server device 122 for processing at the server device 122 to determine whether the implantable device 104 and the external device 116 are experiencing a telemetry connectivity problem (e.g., via server device (SD) connectivity assessment component 606, as discussed infra with respect to FIG. 6).

In another example, the ED reporting component 210 can cache monitored telemetry connectivity information monitored over a defined period of time and send the monitored telemetry connectivity information in the cache to the server device 122 and/or the implantable device 104 after passage of the defined period of time.

In one exemplary embodiment, the ED connectivity monitoring component 204 can monitor telemetry connectivity information associated with reception of advertisement signals from the implantable device 104, referred to herein as "advertisement signal information." For example, the implantable device 104 transmits an advertisement signal including information identifying the implantable device 104 and/or indicating the implantable device 104 is available and ready for performing telemetry communication. In certain implementations, the advertisement signal can be detected by various other devices within transmission range of the implantable device 104 that are also configured to employ the same or similar telemetry communication protocol as the external device 116. In other embodiments, the advertisement signals transmitted by the implantable device 104 can be configured for reception by only the external device 116.

In some implementations, based on reception of an advertisement signal from the implantable device 104, the external device 116 is configured to perform one or more processes that facilitate establishing a telemetry session with the implantable device 104. For example, the external device 116 can send a response to the implantable device 104 that informs the implantable device 104 that the external device 116 detected the advertisement signal and that the external device 116 would like to establish a telemetry communication session with the implantable device 104. After transmission of an advertisement signal, the implantable device 104 can activate the receiver for the implantable device 104 for a defined window of time during which the implantable device 104 can receive the response to the advertisement signal, transmitted by the external device 116. Based on reception of a response to the advertisement signal from the external device 116 (and in some implementations after performance of a pairing/authentication procedure), the implantable device 104 and the external device 116 can establish a telemetry communication session.

In one embodiment, the implantable device 104 is configured to regularly transmit advertisement signals. The number and frequency of the advertisement signals can be fixed and/or can change from time to time. For example, the implantable device 104 can transmit N advertisement signals within M hours. In another example, the implantable device 104 can transmit one advertisement signal every X seconds or minutes. In another implementation, the implantable device 104 can transmit advertisement signals according to a defined schedule or operation mode. For example, the implantable device 104 can transmit advertisement signals at certain defined points throughout a time period (e.g., a 24 hour time period). In another example, the number and frequency of advertisement signals to be transmitted by the implantable device 104 can be based on a particular operation mode of the implantable device 104, wherein the implantable device 104 is configured to operate in different operation modes according to a defined time schedule or based on a trigger event (e.g., detection of biometric information outside a defined range).

In some implementations the implantable device 104 is configured to transmit two types of advertisement signals to the external device 116. The first type includes an advertisement signal referred to as an "alert," and the second type is referred to as a "non-alert." The implantable device 104 can include information with the respective advertisement signals (e.g., a universal unique identifier (UUID)) that identifies the respective signals as either an alert or a non-alert. In some embodiments, the alert and non-alert advertisement signals can be indicative of one or more states of the implantable device 104. The external device 116 is configured to listen for one or more types of advertisement signals. Upon detection/reception of an advertisement signal that indicates a desire for a telemetry session by the implantable device 104, the external device 116 is configured to connect (or attempt to connect) with the implantable device 104, and upon connection, send the implantable device 104 an interrogation request message. The interrogation request message facilitates reading information from the implantable device 104 (e.g., stored in memory of the implantable device 104). For example, the interrogation request message can request that the implantable device 104 send the external device 116 certain information. Upon reception of an interrogation request message, the implantable device 104 is configured to respond by providing the external device 116 with the requested information. The external device 116 can be configured to process the information received from the implantable device 104 and/or forward the information to the server device 122.

A non-alert advertisement signal can facilitate provisioning of information (e.g., configuration information), by the external device 116 to the implantable device 104. For, example, upon reception/detection of a non-alert advertisement signal, the external device 116 can connect (or attempt to connect) with the implantable device 104 if the external device 116 has information to send to the implantable device 104. After a connection is established, the external device 116 can send the implantable device 104 the information.

In various implementations, the server device 122 provides the external device 116 with the information for provision to the implantable device 104. In most scenarios, reception of a non-alert advertisement signal by the external device 116 does not prompt the external device 116 to connect with the implantable device 104. For example, upon reception of a non-alert advertisement signal, the external device 116 can determine whether the server device 122 has a pending downlink for provision, by the external device 116, to the implantable device 104. In response to a determination that the server device 122 does not have a pending downlink, the external device 116 can ignore the non-alert advertisement signal. However, in response to a determination that the server device 122 does have a pending downlink, the external device 116 can receive the downlink from the server device 122 and respond to the non-alert advertisement signal by establishing a connection with the implantable device 104 and sending the downlink to the implantable device 104.

It should be appreciated that telemetry communication protocol parameters regarding number, frequency, type and/or timing of transmission of advertisement signals by the implantable device 104 can vary depending on the application and configuration of the implantable device 104. Similarly the communication protocol parameter values represented herein by variables (e.g., N, M and X) can vary depending on the application and configuration of the implantable device 104. However, the specific telemetry communication parameters (e.g., the number, frequency, type and/or timing of transmission of advertisement signals and the values of N, M and X) to be employed by the implantable device 104 to communicate with the external device 116 are defined.

According to this embodiment, the ED connectivity monitoring component 204 can monitor or log advertisement signal information regarding a number of advertisement signals received by the external device 116. For example, the ED connectivity monitoring component 204 can monitor or log advertisement signal information regarding a number of advertisement signals received by the external device 116 over a defined time period (e.g., 24 hours). The ED connectivity monitoring component 204 can also associate a timestamp received by one or more of the advertisement signals from the implantable device 104. In some implementations, the ED connectivity monitoring component 204 can also monitor the types of advertisement signals that are received (e.g., alert or non-alert).

In other embodiments, the ED connectivity monitoring component 204 is configured to monitor telemetry connectivity information related to successful telemetry connection sessions established between the external device 116 and the implantable device 104, referred to herein as "telemetry session information." For example, as described above, based on reception of an advertisement signal from the implantable device 104, the external device 116 and the implantable device 104 can establish a successful telemetry session. For instance, the external device 116 can send the implantable device 104 a response to the advertisement signal informing the implantable device 104 that the advertisement signal was received (e.g., an acknowledgment signal). Based on reception of the response by the implantable device 104, the implantable device 104 and the external device 116 can establish a telemetry session send and/or receive data packets between one another in accordance with defined applications of the respective devices and defined telemetry communication protocols employed by the respective devices. In another example, based on reception of an alert advertisement signal, the external device 116 can establish a telemetry connection/session with the implantable device 104 to read information from the implantable device 104 (e.g., using an interrogation message and associated protocol). For instance, the implantable device 104 can provide the external device 116 with requested information (e.g., biometric information sensed by the implantable device 104, telemetry connectivity integrity information monitored by the implantable device 104, etc.) in response to an interrogation message sent by the external device 116 to the implantable device 104 requesting the information.

In another example, based on reception of a non-alert advertisement signal, when the external device 116 has information to send to the implantable device 104, the external device 116 can establish a telemetry connection/session with the implantable device 104 and provide the information to the implantable device 104. For instance, the external device 116 can provide the external device 116 with configuration or re-configuration information for application by the implantable device 104. After the respective devices have received and/or transmitted the specific data packets associated with the telemetry connection/session in accordance with the defined telemetry communication protocols employed by the respective devices, the telemetry communication session is ended. The implantable device 104 then returns to transmitting advertisement signals according to the defined telemetry communication protocol employed.

In some implementations, the external device 116 can attempt to establish a successful telemetry session with the implantable device 104 each time the external device 116 receives an advertisement signal from the implantable device 104. In other embodiments, the external device 116 can selectively respond to advertisement signals received from the implantable device 104 according to the configuration and application of the external device 116 in accordance with the defined telemetry communication protocol employed by the external device 116. An unsuccessful telemetry communication session refers to an inability for the external device 116 and the implantable device 104 to establish a successful telemetry session after the external device 116 receives and/or responds to an advertisement signal provided by the implantable device 104. For example, an unsuccessful telemetry session can include a failure, by the implantable device 104 and/or the external device 116 to perform telemetry communication according to the defined telemetry communication protocol following an attempt, by the external device 116 or the implantable device 104, to establish a telemetry session with the implantable device 104 or the external device, respectively.

In accordance with these embodiments, the ED connectivity monitoring component 204 can monitor or log telemetry connectivity information identifying one or more times a successful telemetry session is established between the external device 116 and the implantable device 104 over a defined time period (e.g., a 24 hour period). In some implementations, the ED connectivity monitoring component 204 can also time stamp the successful telemetry sessions and identify the duration (e.g., start time and end time) of the successful telemetry sessions. The ED connectivity monitoring component 204 can also log the occurrence of failed or unsuccessful telemetry sessions following an attempt, by the external device 116 and/or the implantable device 104, to establish a telemetry connection session. For example, the ED connectivity monitoring component 204 can monitor responses sent by the external device 116 to the implantable device 104 following reception of an advertisement signal by the external device 116, and whether a successful telemetry session was established between the implantable device 104 and the external device 116 based on the sending of the respective responses.

In another example, the ED connectivity monitoring component 204 can monitor interrogation signal information identifying when interrogation requests are sent by the external device 116 to the implantable device 104 and whether the external device 116 received a response to the respective interrogation requests. In yet another example, the ED connectivity monitoring component 204 can monitor transmission of configuration or re-configuration information by the external device 116 to the implantable device 104, and whether the external device 116 receives an acknowledgment message, from the implantable device 104, confirming that the configuration information was received and applied by the implantable device 104.

The ED connectivity monitoring component 204 can also monitor or log RSSI information associated with strengths of signals received by the external device 116 from the implantable device 104 and throughput of data packets received from the implantable device 104. For example, the ED connectivity monitoring component 204 can monitor strengths of advertisement signals received by the external device 116 from the implantable device 104. In another example, after the external device 116 and the implantable device 104 have established a successful telemetry session, the ED connectivity monitoring component 204 can monitor strengths of data downlink packets received from the implantable device 104 and throughput of the downlink data packets. The ED connectivity monitoring component 204 can also monitor throughput of uplink packets transmitted by the external device 116 to the implantable device 104.

FIG. 3 illustrates a block diagram of an example, non-limiting table (e.g., table 300 including telemetry connectivity information monitored by an external device in accordance with one or more embodiments described herein. Table 300 includes example telemetry connectivity information monitored by the ED connectivity monitoring component 204 in accordance with embodiments described herein. In the embodiment shown in table 300, the ED connectivity monitoring component 204 monitored telemetry connectivity information for the external device 116 over a 24 hour time period (e.g., time 00:00 to time 24:00 using a 24 hour clock), wherein 10 advertisement signals were received by the external device 116. The first advertisement signal was received at time 10:12 and the tenth advertisement signal was received at time 22:55. It should be appreciated however that the information included in table 300 is merely exemplary. For example, although table 300 demonstrates 10 advertisement signals being received by the external device 116 from times 10:12 to 22:55, it should be appreciated that the external device 116 can receive less or more advertisement signals at different times throughout a 24 hour period. In addition, the number of alert verses non-alert advertisement signals can vary, the number of connections established can vary, the RSSI can vary, etc.

For instance, in one embodiment, based on the telemetry communication protocol scheme employed by the external device 116 and the implantable device 104, the implantable device 104 is configured to send about 480 advertisement signals within a 24 hour period. Based on various configuration settings of the external device, the external device 116 is expected to hear an advertisement signal about 3 percent of the time when the external device 116 and the implantable device 104 are within transmission range of one another. In practice, the external device 116 and the implantable device 104 are expected to be within transmission range of one another for about eight hours of the 24 hour period. According to this embodiment, the external device 116 is expected to receive/detect about five advertisement signals within a 24 hour period. As such, reception/detection of less or much less than five advertisement signals within a 24 hour period can indicate a connectivity issue. While this embodiment has been described with reference to specific values and methodologies, the disclosure and embodiments described herein are not so limited. In fact, in various different embodiments, any number of different values or methodologies can be employed and all such variations are within the scope of the disclosure.

In addition to identifying when respective advertisement signals are received by the external device 116 over a 24 hour time period, table 300 also includes information identifying the type of advertisement signal received (e.g., alert verses non-alert), whether a successful telemetry session or connection was established between the external device 116 and the implantable device 104 based on the received advertisement signal, and RSSI associated with the received advertisement signals (and other possible received signals). For example, the external device 116 received four alert advertisement signals, signals 1, 5, 7 and 9. Among these alert signals, successful telemetry connections/sessions were established between the external device 116 and the implantable device 104 for signals 1, 5, and 9. The external device 116 also established a successful telemetry session with the implantable device based on reception of non-alert signal 10.

For signals 1, 5, and 9, table 300 also includes information identifying whether an interrogation was sent, whether it was successful (e.g., whether the external device received a response from the implantable device 104 with requested information), and the average throughput of the response to successful interrogations. As seen in table 300, although a connection was established and an interrogation was sent based on reception of signal 9, the interrogation was unsuccessful. For successful interrogations, table 300 also includes throughput information (e.g., throughput of downlink information received in response to the interrogation request). Table 300 also includes throughput information associated with uplink information provided by the external device 116 to the implantable device 104 following reception of non-alert signal 10.

Referring back to FIGS. 1 and 2, in various embodiments, the ED connectivity assessment component 206 is configured to evaluate the integrity and/or quality of telemetry connectivity between the external device 116 and the implantable device 104 based on telemetry connectivity information monitored by the ED connectivity monitoring component 204. For example, the ED connectivity assessment component 206 can analyze the telemetry connectivity information monitored by the ED connectivity monitoring component 204 and determine whether a telemetry connectivity error condition exists between the external device 116 and the implantable device 104. In some implementations, described infra, the ED connectivity assessment component can also evaluate the integrity and/or quality of telemetry connectivity between the external device 116 and the implantable device 104 based on telemetry connectivity information monitored by the implantable device 104 (e.g., via ID connectivity monitoring component 404 discussed with respect to FIG. 4).

In one embodiment, the ED connectivity assessment component 206 is configured to determine whether the external device 116 and the implantable device 104 are experiencing a telemetry connectivity error condition based on an amount of advertisement signals received by the external device 116 from the implantable device 104 within a defined time period. According to this embodiment, the ED connectivity assessment component 206 can analyze the monitored telemetry connectivity information after passage of the defined time period. For example, the implantable device 104 can transmit N (e.g., 480) advertisement signals within a defined time period of X hours (e.g., 24 hours). The ED connectivity assessment component 206 can further determine that the external device 116 and the implantable device 104 are experiencing a telemetry connectivity error condition if the number of the advertisement signals received by the external device 116 within the defined time period is below a threshold value (e.g., 5, 10, 20, etc.). In another example, the ED connectivity assessment component 206 can determine that a telemetry connectivity error condition associated with telemetry communication between the external device 116 and the implantable device 104 exists based on the number of advertisement signals received by the external device 116 exceeding the threshold value or another threshold value.

In another embodiment, the ED connectivity assessment component 206 is configured to determine whether the external device 116 and the implantable device 104 have a connectivity problem based on timing of advertisement signals received by the external device 116 from the implantable device 104. According to this embodiment, the ED connectivity assessment component 206 can regularly analyze the monitored telemetry connectivity information as it is received. For example, when the implantable device 104 is configured to transmit advertisement signals at a particular frequency (e.g., about one signal per minute), the ED connectivity assessment component 206 can determine that the external device 116 and the implantable device 104 have a telemetry connectivity problem if the frequency of the advertisement signals received by the external device 116 falls above or below the particular frequency (e.g., with respect to a defined deviation threshold). In another example, when the implantable device 104 is configured to transmit advertisement signals according to a defined time schedule, the ED connectivity assessment component 206 can determine that telemetry communication between the external device 116 and the implantable device 104 is associated with a telemetry connectivity error condition if the external device 116 fails to receive advertisement signals from the implantable device 104 in accordance with the defined time schedule.

In some implementations, the ED connectivity assessment component 206 can also analyze type of advertisement signal received to identify connectivity issues. With these implementations, the amount, frequency and/or timing of alert signals and non-alert signals for transmission implantable device 104 within a defined time period can be defined. The ED connectivity assessment component 206 can identify connectivity issues based on the amount, frequency, and/or timing of received alert advertisement signals and/or the non-alert advertisement signals by the external device 116 from the implantable device 104 failing to comply with the defined parameters for reception of these signals. The ED connectivity assessment component 206 can also be configured to determine whether the external device 116 and the implantable device 104 have a connectivity problem based on an amount of successful telemetry sessions established between the external device 116 and the implantable device 104 with a defined time period (e.g., 1 hour, 3 hours, 12 hours, 24 hours, etc.). For example, when the implantable device 104 and the external device 116 are configured to establish about M successful telemetry session within the defined time period, the ED connectivity assessment component 206 can determine that that the external device 116 and the implantable device 104 have a telemetry connectivity problem if the external device 116 and the implantable device establish less than a threshold number (e.g., M or another number) of successful telemetry sessions within the defined time period.

In another implementation, the ED connectivity assessment component 206 can identify occurrence of a telemetry connectivity error condition associated with performance of telemetry communication between the external device 116 and the implantable device 104 based on an amount of successful telemetry sessions established between the implantable device 104 and the external device 116 within a defined period of time relative to an amount of advertisement signals received by the external device within the defined period of time. For example, the ED connectivity assessment component 206 can determine that a connectivity error condition exists based on a determination that a ratio or percentage of the amount of successful telemetry sessions established relative to the amount of advertisement signals received is below a threshold ratio or threshold percentage (e.g., 25%, 15%, 10%, 5%, 3%, etc.). The ED connectivity assessment component 206 can similarly compare a ratio of successful telemetry connections established relative to an amount of alert or non-alert advertisement signals received to a threshold ratio or percentage to identify a connectivity issue.

Similarly, the ED connectivity assessment component 206 can determine whether the external device 116 and the implantable device 104 have a connectivity problem based on an amount of successful interrogations sent be the external device 116 to the implantable device 104 within a defined time period (wherein a successful interrogation refers to reception, by the external device 116, of information requested from the implantable device 104). For example, the ED connectivity assessment component 206 can determine that a telemetry communication error condition exists between the external device 116 and the implantable device 104 based on a number of successful interrogations during a defined time period relative to a threshold amount. For example, the ED connectivity assessment component 206 can determine that telemetry communication between the external device 116 and the implantable device 104 is affected by a connectivity error condition in cases in which the interrogation success rate for a defined time period falls below a threshold value. According to this example, the interrogation success rate can refer to number of successful interrogations relative to number of alert advertisement signals received, or number of successful interrogations relative to number of interrogation requests sent.

In various additional embodiments, the ED connectivity assessment component 206 can also determine whether a telemetry connectivity error condition associated with telemetry communication between the external device 116 and the implantable device 104 exists based on RSSI information for signals received by the external device 116 from the implantable device 104. For example, the ED connectivity assessment component 206 can determine that the external device 116 and the implantable device 104 have a telemetry connectivity problem based on the RSSI information indicating the average strength of signals received by the external device 116 from the implantable device 104 within a defined time period is below a threshold value. In another example, the ED connectivity assessment component 206 can identify occurrence of telemetry connectivity error conditions based on a drop in strengths of signals received by the external device 116 from the implantable device 104. In another example, the ED connectivity assessment component 206 can identify connectivity problems based on identification of a distinguishable pattern associated with strengths of different signals received by the external device 116 from the implantable device 104 that are indicative of a connectivity problem. In yet another example, the ED connectivity assessment component 206 can determine that the external device 116 and the implantable device 104 have a telemetry connectivity problem based on significant variation (e.g., with respect to a defined variation range) in RSSI information for different signals received by the external device 116 within a defined time period.

In another embodiment, the ED connectivity assessment component 206 can determine whether the external device 116 and the implantable device 104 have a connectivity problem based on throughput of downlink data packets received by the external device 116 from the implantable device 104, and uplink data packets sent by the external device 116 to the implantable device. For example, the ED connectivity assessment component 206 can determine that a connectivity error condition associated with telemetry communication between the external device 116 and the implantable device 104 exists based on downlink throughput information indicating the average throughput of data packets received by the external device 116 from the implantable device 104 within a defined time period is below a threshold value. In another example, the ED connectivity assessment component 206 can determine that the external device 116 and the implantable device 104 have a telemetry connectivity problem based on a defined variation (e.g., with respect to a variation range) in downlink throughput information for different data packets received by the external device 116 within a defined time period. In another example, the ED connectivity assessment component 206 can determine that a connectivity error condition associated with telemetry communication between the external device 116 and the implantable device 104 exists based on uplink throughput information indicating the average throughput of data packets transmitted by the external device 116 to the implantable device 104 within a defined time period is below a threshold value.

In some embodiments, the ED connectivity assessment component 206 can also diagnose a cause of an identified telemetry connectivity problem based on telemetry connectivity information monitored by ED connectivity monitoring component 204 (and in some implementations, based on telemetry connectivity information monitored at the implantable device 104 and provided to the external device 116 by the implantable device 104). For example, based on the monitored telemetry connectivity information, the ED connectivity assessment component 206 can determine whether a telemetry connectivity problem between the external device 116 and the implantable device is attributed to a hardware malfunction at the external device 116, a hardware malfunction at the implantable device 104, a software configuration problem at the external device 116, a software configuration problem at the implantable device 104, and/or an interference problem associated with the communication channel between the external device 116 and the implantable device 104. In another example, the ED connectivity assessment component 206 can determine whether a telemetry connectivity problem is attributed to failure of the external device 116 to be within telemetry transmission range of the implantable device 104 for a minimum amount of time (e.g., 8 hours) within a defined time period (e.g., 24 hours).

The ED notification component 208 facilitates notification to users (via user devices) regarding a telemetry connectivity problem determined to exist between the external device 116 and the implantable device 104. In one embodiment, the ED notification component 208 is configured to generate a notification based on detection, by ED connectivity assessment component 206, of a telemetry connectivity problem between the external device 116 and the implantable device 104. The notification can include information indicating the implantable device 104 and the external device 116 are experiencing a telemetry connectivity problem. In some embodiments, the notification can also include information identifying a cause of the telemetry connectivity problem or a potential solution to the telemetry connectivity problem. For example, many identified telemetry connectivity issues are attributed to failure of the external device 116 to remain within wireless transmission range of the implantable device 104 for a minimum amount of time within a monitored time period. According to this example, the notification can include information that instructs the wearer of the implantable device 104 to move within transmission proximity of the external device 108 for a least a minimum amount of time.

In some implementations, the ED notification component 208 is further configured to present or render the notification at the external device 116. For example, ED notification component 208 can present a visual notification at the external device 116 that informs a user of the external device 116 (e.g., the wearer of the implantable device 104) regarding the connectivity problem. According to this example, the visual notification can include text, an image, a symbol, etc., presented via a display screen of the external device 116. In another example, the visual notification can include an illuminated or blinking light at the external device 116 that indicates the connectivity problem. In another example, the ED notification component 208 can generate an audible notification at the external device 116 via a speaker of the external device 116 that informs the user regarding the connectivity problem. For example, the notification can include an alarm or sound that requires manual interaction with the external device 116 to disable the external device 116 (e.g., via the wearer of the implantable device 104). Still in yet another example, the notification can include a vibration generated at the external device 116.

In another implementation, in addition or in the alternative to rendering the notification at the external device 116, the ED notification component 208 can send the notification to the server device 122. For example, the server device 122 can be associated with a remote medical monitoring service that can inform a remote device associated with a medical caregiver regarding the connectivity problem between the implantable device 104 and the external device 116 based on reception of the notification from the ED notification component 208.

Figure 4:
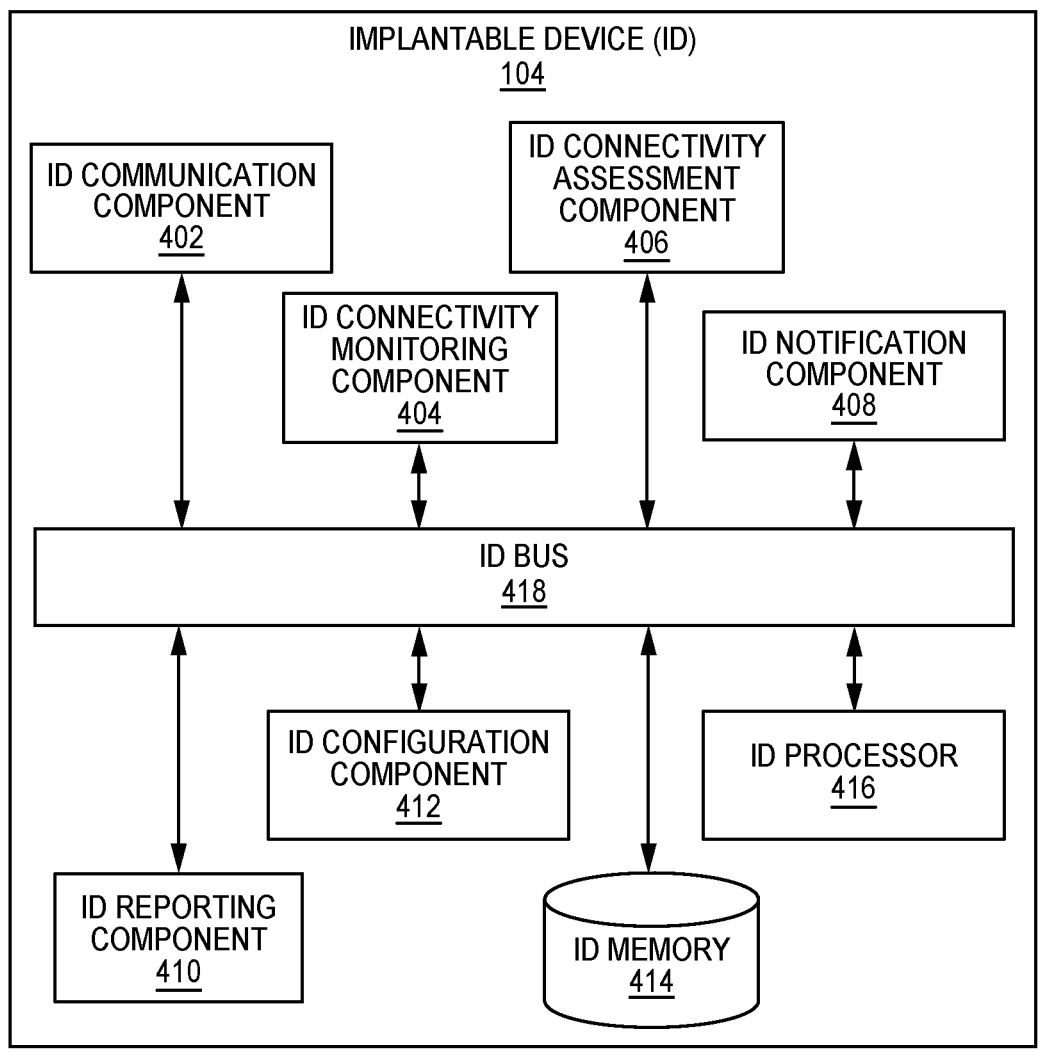
FIG. 4 illustrates a block diagram of an example, non-limiting implantable device for which integrity of telemetry connectivity with an external device is monitored in accordance with one or more embodiments described herein.
Figure 6:
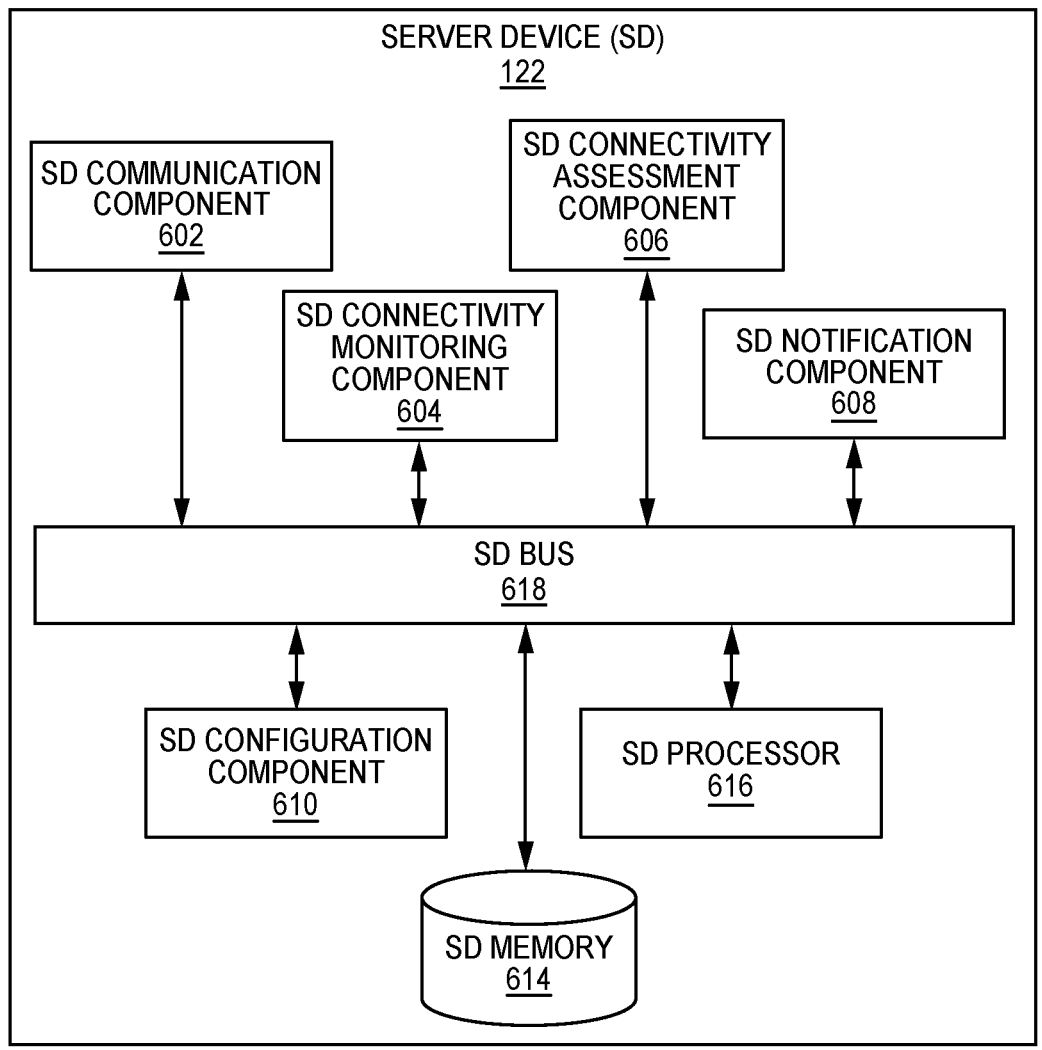
FIG. 6 illustrates a block diagram of an example, non-limiting server device in accordance with one or more embodiments described herein.

In some embodiments, the external device 116 and/or the implantable device 104 can be reconfigured to correct a telemetry connectivity error condition identified between the external device 116 and the implantable device 104 (e.g., as identified via the ED connectivity assessment component 206, the implantable device 104 via implantable device (ID) connectivity assessment component 406 discussed infra with respect to FIG. 4, and/or the server device 122 via SD connectivity assessment component 606, discussed infra with respect to FIG. 6). According to these embodiments, the external device 116 can include ED configuration component 212 to facilitate reconfiguring the external device 116 and/or the implantable device 104 to correct the telemetry connectivity problem.

In one embodiment, the ED configuration component 212 is configured to apply reconfiguration information received from the server device 122. According to this implementation, the server device 122 can determine how to reconfigure the external device 116 including, but not limited to, correct an identified telemetry connectivity problem between the implantable device 104 and the external device 116 (e.g., via SD configuration component 612, as discussed infra with respect to FIG. 6). For example, the server device 122 can send the external device 116 reconfiguration information that includes instructions regarding how external device 116 should be reconfigured. The external device 116 can also receive a command from the server device 122 in association with reception of the reconfiguration information that instructs the external device 116 to apply the reconfiguration information. In response to reception of the reconfiguration information and the command from the server device 122, the ED configuration component 212 can apply the reconfiguration information. In another embodiment, the ED configuration component 212 and/or the ED communication component 202 is configured to relay implantable device reconfiguration information, received from the server device 122, to the implantable device 104.

In additional embodiments, in response to a determination (e.g., by the ED connectivity assessment component 206) that a connectivity problem between the external device 116 and/or the implantable device 104 is based on telemetry communication protocol configuration settings of the external device 116 and/or the implantable device 104, the ED configuration component 212 or server device 122 can generate information to cause one or more configuration settings to be updated or the ED configuration component 212 can generate information to cause one or more operations to be altered.

For example, the ED configuration component 212 can modify a number of data packets per connection interval that the external device 116 should send to the implantable device 104 and/or a number of data packets per connection interval that the implantable device 104 should send the external device 116. In another example, the ED configuration component 212 can change the duration of for which the implantable device 104 and the external device 116 should maintain a connection in association with an established telemetry session (i.e., modify the connection interval).

In one embodiment, the ED configuration component 212 can further automatically update telemetry communication protocol parameters employed by the external device 116 and/or the implantable device 104 based on the mechanisms determined to correct the telemetry communication protocols employed by the respective devices. For example, the ED configuration component 212 can direct the external device 116 to update its telemetry communication protocol settings to increase a connection interval between the external device 116 and the implantable device 104. Including, but not limited to, updating the telemetry communication protocols employed by the implantable device 104, the ED configuration component 212 can send the implantable device 104 reconfiguration information that defines how the implantable device should update its telemetry protocol parameters. The reconfiguration information can further direct the implantable device 104 to apply the reconfiguration information to update its telemetry protocol settings.

FIG. 4 illustrates a block diagram of an example, non-limiting implantable device (e.g., implantable device 104) for which integrity of telemetry connectivity with an external device is monitored in accordance with one or more embodiments described herein. The implantable device 104 includes implantable device (ID) communication component 402, an ID connectivity monitoring component 404, an ID connectivity assessment component 406, an ID notification component 408, an ID reporting component 410, and an ID configuration component 412. In various embodiments described herein, the components of implantable device 104 can perform same or similar functions as the corresponding components of the external device 116. For example, with reference to FIGS. 2 and 4, the ID communication component 402 can perform same or similar functions as ED communication component 202, the ID connectivity monitoring component 404 can perform same or similar functions as ED connectivity monitoring component 204, the ID connectivity assessment component 406 can perform same or similar functions as ED connectivity assessment component 206, the ID notification component 408 can perform same or similar functions as the ED notification component 208, the ID reporting component 410 can perform same or similar functions as the ED reporting component 210, and the ID configuration component 412 can perform same or similar functions as the ED configuration component 212.

One or more of the components of implantable device 104 constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The implantable device 104 can include ID memory 414 for storing the computer executable components and instructions, and ID processor 416 to facilitate operation of the computer executable components and instructions by implantable device 104. The implantable device 104 can include an ID bus 418 that couples the various components of the implantable device 104, including, but not limited to, the ID communication component 402, the ID connectivity monitoring component 404, the ID connectivity assessment component 406, the ID notification component 408, the ID reporting component 410, the ID configuration component 412, the ID processor 416 and/or the ID memory 414. Repetitive description of like elements employed in other embodiments described herein is omitted for sake of brevity.

With reference to FIGS. 1, 2 and 4, similar to the ED communication component 202, the ID communication component 402 can facilitate telemetry communication between the implantable device 104 and the external device 116. For example, the ID communication component 402 can include or be various hardware and software devices associated with establishing and/or conducting a telemetry communication between the implantable device 104 and the external device 116. For example, ID communication component 402 can control operation of a transmitter-receiver or transceiver (not shown) of the implantable device 104 to establish a telemetry session with the external device 116 and to control transmission and reception of signals or data packets between the implantable device 104 and the external device 116.

The ID communication component 402 can facilitate telemetry communication between the implantable device 104 and the external device using a variety of telemetry communication protocols. For example, the ID communication component 402 can communicate with the external device 116 using communication protocols including, but not limited to, a NFC based protocol, a BLUETOOTH® technology-based protocol, a ZigBee® based protocol, a WirelessHART® based protocol, a Z-Wave® based protocol, an ANT based protocol, an RF based communication protocol, an IP based communication protocol, a cellular communication protocol, a UWB technology-based protocol, or other forms of communication including both proprietary and non-proprietary communication protocols.

In various embodiments, the ID communication component 402 is configured to control transmission and reception of information between the implantable device 104 and the external device 116 via a telemetry communication link (e.g., telemetry communication link 118) facilitated by a communication protocol utilizing lower energy consumption than a conventional communication protocol for wirelessly transmitting data. In a non-limiting example, the ID communication component 402 controls transmission and reception of signals and data packets between the implantable device 104 and the external device 116 using BLE protocol.

Similar to the ED connectivity monitoring component 204, the ID connectivity monitoring component 404 is configured to monitor telemetry connectivity information associated with the integrity and quality of telemetry connectivity between the implantable device 104 and the external device 116. For example, after establishing an initial connection with the external device 116, pairing with the external device 116, or otherwise establishing an authorized telemetry communication link (e.g., a telemetry communication link 118) with the external device 116, the ID connectivity monitoring component 404 can monitor telemetry connectivity information associated with telemetry communication between the implantable device 104 and the external device 116 over the course of operation of the implantable device 104. In another example, the ID connectivity monitoring component 404 can monitor telemetry connectivity information associated with telemetry communication between the implantable device 104 and the external device 116 according to a temporal cycle or schedule. For instance, the ID connectivity monitoring component 404 can monitor or track telemetry connectivity information for a defined period of time each hour, 3 hours, 12 hours, 24 hours, etc. In yet another example, the ID connectivity monitoring component 404 can randomly monitor telemetry connectivity information associated with telemetry communication between the implantable device 104 and the external device 116.

Still in yet another example, the ID connectivity monitoring component 404 can monitor telemetry connectivity information in response to a request command received from the external device 116. According to this example, the request can be associated with a request to perform an assessment on the quality and integrity of telemetry connectivity between the implantable device 104 and the external device 116. The request can define a type of telemetry connectivity information for the ID connectivity monitoring component 404 to monitor and period of time over which the ID connectivity monitoring component 404 is to monitor the telemetry connectivity information. In one embodiment, the request command can be issued based on user input at the external device 116 identifying the type of telemetry connectivity information for the ID connectivity monitoring component 404 to monitor and the time period over which ID connectivity monitoring component 404 should monitor the telemetry connectivity information. In another implementation, the request command can be issued by the server device 122. According to this implementation, the request command can be transmitted by the server device 122 to the external device 116 via communication link 120 and further related by the external device 116 to the implantable device 104 via telemetry communication link 118.

In some embodiments, the implantable device 104 can log or store the telemetry connectivity information monitored by the ID connectivity monitoring component 404 in ID memory 414. The ID connectivity monitoring component 404 can remove all or portions of the logged telemetry connectivity information over time for replacement with new telemetry connectivity information. In other embodiments, in addition or in the alternative to storing the telemetry connectivity information in ID memory 414, the implantable device 104 can send the monitored telemetry connectivity information to the external device 116 and/or the server device 122 via ID reporting component 410 and/or ID communication component 402. According to these embodiments, the telemetry connectivity information monitored by the ID connectivity monitoring component 404 can be employed by the external device 116 and/or the server device 122 for analysis and evaluation of telemetry connectivity problems between the implantable device 104 and the external device 116.

For example, the ID reporting component 410 and/or the ID communication component 402 can send telemetry connectivity information monitored by the ID connectivity monitoring component 404 to the external device 116 according to a defined schedule (e.g., once an hour, once a day, twice a day, etc.). In another example, the ID reporting component 410 and/or the ID communication component 402 can send telemetry connectivity information monitored by the ID connectivity monitoring component 404 to the external device 116 in response to a request (e.g., an interrogation request), received from the external device 116 for the telemetry connectivity information. The external device 116 can further forward telemetry connectivity information received from the implantable device 104 to the server device 122 (e.g., via ED reporting component 210 and/or ED communication component 202).

In one exemplary embodiment, the ID connectivity monitoring component 404 is configured to monitor telemetry connectivity information associated with transmission of advertisement signals from the implantable device 104 to the external device 116, (also referred to herein as advertisement signal information). As described supra, the number, frequency, type and/or timing of transmission of the advertisement signals can be defined and can vary from time to time. According to this embodiment, the ID connectivity monitoring component 404 can monitor or log advertisement signal information regarding number, frequency, type and/or timing of advertisement signals transmitted by the implantable device 104. For example, the ID connectivity monitoring component 404 can monitor or log advertisement signal information regarding a number of advertisement signals transmitted by the implantable device 104 over a defined time period (e.g., 24 hours). The ID connectivity monitoring component 404 can also associate a timestamp with each advertisement signal transmitted by the implantable device 104. The ID connectivity monitoring component 401 can also identify the types (e.g., alert or non-alert) of advertisement signals sent.

In other embodiments, the ID connectivity monitoring component 404 is configured to monitor telemetry connectivity information related to amount, frequency and/or timing of successful telemetry connection sessions established between the implantable device 104 and the external device 116. Similarly, the ID connectivity monitoring component 404 can also log the amount, frequency, and/or timing of failed or unsuccessful telemetry sessions following an attempt, by the external device 116 and/or the implantable device 104, to establish a telemetry connection session. The ID connectivity monitoring component 404 can also monitor or log RSSI information associated with strengths of signals received by the implantable device 104 from the external device 116, throughput of downlink data packets received from the external device 116, and throughput of uplink data packets transmitted to the external device 116. For example, the ID connectivity monitoring component 404 can monitor strengths of advertisement response signals received from the external device 116. In another example, after the external device 116 and the implantable device 104 have established a successful telemetry session, the ID connectivity monitoring component 404 can monitor strengths of data packets received from the external device 116 and throughput of the data packets.

FIG. 5 illustrates a block diagram of an example, non-limiting table (e.g., table 500) including telemetry connectivity information monitored by an implantable device (e.g., implantable device 104) in accordance with one or more embodiments described herein. The table 500 includes some example telemetry connectivity information monitored by the ID connectivity monitoring component 404 in accordance with embodiments described herein. In the embodiment exemplified in table 500, the ID connectivity monitoring component 404 monitored telemetry connectivity information for the implantable device 104 over a 24 hour time period (e.g., time 00:00 to time 24:00 using a 24 hour clock), wherein 20 advertisement signals were transmitted by the implantable device 104. The first advertisement signal was transmitted at time 10:05 and the tenth advertisement signal was received at time 22:51. It should be appreciated however that the information included in table 500 is merely exemplary. For example, although table 500 demonstrates 20 advertisement signals being transmitted from the implantable device from times 10:05 to 22:51, it should be appreciated that the implantable device 104 can transmit different amounts of advertisement signals at different times throughout a 24 hour period. For example, in one embodiment, the implantable device 104 is configured to transmit between 300 and 600 advertisement signals a day. In another embodiment, the implantable device 104 is configured to transmit between 450 and 550 advertisement signals a day. In yet another embodiment, the implantable device 104 is configured to transmit about 480 advertisement signals a day. In addition, the number of alert verses non-alert advertisement signals can vary, the number of connections established can vary, the RSSI can vary, etc.

In addition to identifying when respective advertisement signals are sent by the implantable device 104 over a 24 hour time period, table 500 also includes information identifying the type of advertisement signal received (e.g., alert verses non-alert), and whether a successful telemetry session or connection was established between the external device 116 and the implantable device 104 based on the transmitted advertisement signal. For example, successful telemetry sessions were established between the external device 116 and the implantable device 104 based on transmission of advertisement signals 1, 9, 17 and 19. For connections based on signals 1 and 9, interrogations signals were received and responded to by implantable device 104. For these signals information is recorded that identifies RSSI associated with signals received from the external device 116 (e.g., the interrogation requests), and throughput of interrogation response data packets transmitted by the implantable device 104. Although a connection was established and an interrogation response was received for signal 17, due to some reason (e.g., an error condition such as low RSSI associated with the interrogation request), the implantable device 104 did not send a response. Table 500 also shows that a connection was established based on non-alert signal 19. For this signal, the implantable device 104 recorded RSSI and throughput for downlink information received from the external device 116.

Referring back to FIGS. 1, 2 and 4, in some embodiments, the ID connectivity assessment component 406 is configured to evaluate the integrity and/or quality of telemetry connectivity between the external device 116 and the implantable device 104 based on the telemetry connectivity information monitored by the ID connectivity monitoring component 404. In other embodiments, the implantable device 104 is configured to send telemetry connectivity information monitored by the ID connectivity monitoring component 404 to the external device 116 and/or the server device 122 for evaluation. Still in other embodiments, the ID connectivity assessment component 406 is configured to evaluate the integrity and/or quality of telemetry connectivity between the external device 116 and the implantable device 104 based on the telemetry connectivity information monitored by the ID connectivity monitoring component 404 and telemetry connectivity information monitored by the ED connectivity monitoring component 204 and sent to the implantable device 104 by the external device 116.

For example, based on monitored telemetry connectivity information (e.g., monitored by the ED connectivity monitoring component 204 and/or the ID connectivity monitoring component 404), the ID connectivity assessment component 406 can determine whether the implantable device 104 and the external device 116 have established or maintained establishment of telemetry communication link 118. In another example, the ID connectivity assessment component 406 can determine whether the respective devices can receive data packets from one another with sufficient throughput and/or signal strength via the telemetry communication link 118. In yet another example, the ID connectivity assessment component 406 can determine whether the respective devices can transmit and/or receive information to/from one another via the telemetry communication link 118 according to a defined communication scheme, schedule, or mode of operation.

In one embodiment, the ID connectivity assessment component 406 is configured to determine whether a connectivity error condition associated with telemetry communication between the implantable device 104 and the external device 116 exists based on an amount of advertisement signals transmitted by the implantable device 104 within a defined time period. According to this embodiment, the ID connectivity assessment component 406 can analyze the monitored telemetry connectivity information after passage of the defined time period. For example, the implantable device 104 can transmit N (e.g., 480) advertisement signals within a defined time period of X hours (e.g., 24 hours) or minutes. The ID connectivity assessment component 406 can determine that the external device 116 and the implantable device 104 have a telemetry connectivity problem if the number of the advertisement signals transmitted by the implantable device 104 within the defined time period is below a threshold value (e.g., N or another number). In another example, the ID connectivity assessment component 406 can determine that the external device 116 and the implantable device 104 have a telemetry connectivity problem if the number of advertisement signals transmitted by the implantable device within the defined time period exceeds the threshold value or another threshold value.

In another embodiment, the ID connectivity assessment component 406 is configured to determine whether the external device 116 and the implantable device 104 have a connectivity problem based on timing of advertisement signals transmitted by the implantable device 104. According to this embodiment, the ID connectivity assessment component 406 can regularly analyze the monitored telemetry connectivity information as it is received or determined. For example, when the implantable device 104 is configured to transmit advertisement signals at a particular frequency (e.g., about one signal per minute), the ID connectivity assessment component 406 can determine that the external device 116 and the implantable device 104 have a telemetry connectivity problem if the frequency of the advertisement signals transmitted by the implantable device 104 falls significantly above or below the particular frequency (e.g., with respect to a defined deviation threshold). In another example, when the implantable device 104 is configured to transmit advertisement signals according to a defined time schedule, the ID connectivity assessment component 406 can determine that the external device 116 and the implantable device 104 have a telemetry connectivity problem if the implantable device 104 fails to transmit the advertisement signals in accordance with the defined time schedule.

In some implementations, the ID connectivity assessment component 406 can also analyze type of advertisement signal transmitted to identify connectivity issues. With these implementations, the amount, frequency and/or timing of alert signals and non-alert signals for transmission within a defined time period can be defined. The ID connectivity assessment component 406 can identify connectivity issues based on the amount, frequency, and/or timing of transmitted alert advertisement signals and/or the non-alert advertisement signals by the implantable device 104 failing to comply with the defined parameters for reception of these signals (e.g., being above or below respective threshold amounts for the different types of advertisement signals).

In another exemplary embodiment, the ID connectivity assessment component 406 can also be configured to detect occurrence of a telemetry connectivity error condition associated with telemetry communication between the external device 116 and the implantable device 104 based on an amount of successful telemetry sessions established between the external device 116 and the implantable device 104 with a defined time period (e.g., 1 hour, 3 hours, 12 hours, 24 hours, etc.). For example, when the implantable device 104 and the external device 116 are configured to establish M successful telemetry session within the defined time period, the ID connectivity assessment component 406 can determine that that the external device 116 and the implantable device 104 have a telemetry connectivity problem if the external device 116 and the implantable device establish less than a threshold number (e.g., M or another number) of successful telemetry sessions within the defined time period.

In one embodiment of this embodiment, the ID connectivity assessment component 406 is configured to determine whether the implantable device 104 and the external device 116 have a telemetry connectivity problem based on a ratio or percentage corresponding to the number of successful telemetry sessions established between the implantable device 104 and the external device 116 relative to a number of advertisement signals transmitted (e.g., alert signals and/or non-alert signals) by the implantable device 104 within a defined time period. This ratio or percentage is referred to herein as the "telemetry connectivity session success rate." For example, the implantable device 104 can have an expected telemetry connectivity session success rate of Y percent (e.g., 2%, 3%, 5%, 10%, 15%, etc.). In an embodiment, the ID connectivity assessment component 406 is configured to determine that the implantable device 104 and the external device 116 have a telemetry connectivity problem based on the telemetry connectivity success rate being below or significantly below (e.g., with respect to a threshold degree of deviation), a threshold telemetry connectivity session success rate.

Similarly, the ID connectivity assessment component 406 can determine whether the external device 116 and the implantable device 104 have a connectivity problem based on an amount of interrogations received by the implantable device 104 from the external device 116 within a defined time period. For example, the external device 116 can transmit about N interrogation requests to the implantable device 104 within a defined time period. According to this example, the ID connectivity assessment component 406 can determine that the external device 116 and the implantable device 104 have a telemetry connectivity problem if the amount of interrogation requests received by the implantable device 104 from the external device within the defined time period falls below a threshold value (e.g., N or another number less than N). In another implementation, the ID connectivity assessment component 406 is configured to determine whether a telemetry connectivity problem exists between the external device 116 and the implantable device 104 based on a ratio or percentage corresponding to the amount of interrogation signals received by the implantable device 104 within a defined time period relative to the amount of successful telemetry sessions established between the external device and the implantable device within the defined time period. For example, the ID connectivity assessment component can determine a connectivity error condition associated with telemetry communication between the external device 116 and the implantable device 104 exists if this ratio or percentage is below a threshold ratio or threshold percentage.

In various additional embodiments, the ID connectivity assessment component 406 can also determine whether the external device 116 and the implantable device have a telemetry connectivity problem based on RSSI information for signals received by the implantable device 104 from the external device 116. For example, the ID connectivity assessment component 406 can determine that the external device 116 and the implantable device 104 have a telemetry connectivity problem based on the RSSI information indicating the average strength of signals received by the implantable device 104 from the external device 116 within a defined time period is below a threshold value. In another example, the ID connectivity assessment component 406 can determine that the external device 116 and the implantable device 104 have a telemetry connectivity problem based on significant variation (e.g., with respect to a threshold variation range) in RSSI information for different signals received by the implantable device 104 within a defined time period.

In another embodiment, the ID connectivity assessment component 406 can determine whether the external device 116 and the implantable device 104 have a connectivity problem based on throughput of data packets received by the implantable device 104 from the external device 116. For example, the ID connectivity assessment component 406 can determine that the external device 116 and the implantable device 104 have a telemetry connectivity problem based on throughput information indicating the average throughput of data packets received by the implantable device 104 from the external device within a defined time period is below a threshold value. In another example, the ID connectivity assessment component 406 can determine that the external device 116 and the implantable device 104 have a telemetry connectivity problem based on significant variation (e.g., with respect to a variation range) in throughput information for different data packets received by the implantable device within a defined time period.

In some embodiments, the ID connectivity assessment component 406 can also diagnose a cause of an identified telemetry connectivity problem based on telemetry connectivity information monitored by the ID connectivity monitoring component 404 (and in some implementations, additional telemetry connectivity information monitored by the ED connectivity monitoring component 204).

With reference to FIGS. 1-5, in various embodiments, the telemetry connectivity information monitored by the external device 116 (e.g., via ED connectivity monitoring component 204) and the implantable device 104 (e.g., via ID connectivity monitoring component 404) can be combined and evaluated to determine whether a connectivity problem exists between the implantable device 104 and the external device 116. The analysis of the combined information can be performed at the external device 116 (e.g., via ED connectivity assessment component 206), the implantable device 104 (e.g., via ID connectivity assessment component 406), and/or at the server device (e.g., via SD connectivity assessment component 606, as discussed infra with respect to FIG. 6). In instances in which analysis of the combined telemetry connectivity information is performed at the external device 116 and/or the server device 122, the implantable device 104 can send the external device 116 telemetry connectivity information monitored by the ID connectivity monitoring component 404. For example, the implantable device 104 can report out monitored telemetry connectivity information to the external device using ID reporting component 410 and/or ID communication component 402. In embodiments in which the analysis of the combined telemetry connectivity information is performed at the server device 122, the external device 116 can send (e.g., via ED reporting component 210 and/or ID communication component 402) telemetry connectivity information received from the implantable device 104, and telemetry connectivity information monitored by the ED connectivity monitoring component 204, to the server device 122 via communication link 120.

In accordance with these embodiments, the ED connectivity assessment component 206, the ID connectivity assessment component 406, and/or the SD connectivity assessment component 606, respectively, can compare monitored ED telemetry connectivity information with monitored ID telemetry connectivity information to determine whether the external device 116 and the implantable device 104 have a telemetry connectivity problem. In some embodiments, the respective connectivity assessment components can also determine a cause of an identified telemetry connectivity problem (e.g., configuration problem, hardware problem, interference problem, etc.) based on comparison of the monitored ED telemetry connectivity information with the monitored ID telemetry connectivity information.

In one embodiment, the ED connectivity assessment component 206, the ID connectivity assessment component 406, and/or the SD connectivity assessment component 606 can compare advertisement signal information regarding number, frequency and timing of advertisement signals transmitted by the implantable device 104 to the external device 116 and/or number, frequency and time of advertisement signals received by the external device 116 from the implantable device. The respective telemetry connectivity assessment components can further determine that a telemetry connectivity problem exists between the implantable device 104 and external device 116 based on a degree of incongruency between the information. For example, the respective telemetry connectivity assessment components can determine that a telemetry connectivity problem exists between the implantable device 104 and the external device when the number of advertisement signals transmitted by the implantable device 104 does not correspond or sufficiently correspond (e.g., with respect to a threshold degree of deviation) to the number of advertisement signals received by the external device 116. In another example, the respective telemetry connectivity assessment components can determine that a telemetry connectivity problem exists between the implantable device 104 and the external device 116 in cases in which the frequency and/or timing of advertisement signals transmitted by the implantable device 104 does not correspond or sufficiently correspond (e.g., with respect to a threshold degree of deviation) to the frequency and/or timing of advertisement signals received by the external device 116.

In another implementation, the ED connectivity assessment component 206, the ID connectivity assessment component 406, and/or the SD connectivity assessment component 606 can compare interrogation signal information regarding number, frequency and timing of interrogation signals transmitted by the external device to the implantable device 104 and number, frequency and time of interrogation signals received by the implantable device 104 from the external device 116. The respective telemetry connectivity assessment components can further determine that a telemetry connectivity problem exists between the implantable device 104 and the external device 116 in cases in which the number, frequency and/or timing of interrogation signals transmitted by the external device 116 does not correspond or sufficiently correspond (e.g., with respect to a threshold degree of deviation) to the number, frequency and/or timing of interrogation signals received by the implantable device 104.

Still in yet another implementation, the ED connectivity assessment component 206, the ID connectivity assessment component 406, and/or the SD connectivity assessment component 606 can compare RSSI information for signals received by the external device 116 from the implantable device 104 with RSSI information for other signals received by the implantable device 104 from the external device 116. The respective telemetry connectivity assessment components can further determine that a telemetry connectivity problem exists between the implantable device 104 and the external device 116 in cases in which the RSSI information for signals received by the external device 116 from the implantable device 104 does not correlate or sufficiently correlate (e.g., with respect to a threshold degree of deviation) with the RSSI information for other signals received by the implantable device 104 from the external device 116.

Referring back to FIGS. 1, 2 and 4, similar to the ED notification component 208, the ID notification component 408 facilitates notifying users regarding a telemetry connectivity problems determined to exist between the external device 116 and the implantable device 104. In one embodiment, the ID notification component 408 is configured to generate a notification based on detection, by ID connectivity assessment component 406, of a telemetry connectivity problem between the external device 116 and the implantable device 104. The notification can include information indicating the implantable device 104 and the external device 116 are experiencing a telemetry connectivity problem. In some embodiments, the notification can also include information identifying a cause of the telemetry connectivity problem. In one embodiment, the ID notification component 408 is further configured to send the notification to the external device 116 for rendering or presenting at the external device (e.g., via ED notification component 208). In another embodiment, the ID notification component can send the notification to the external device 116 for forwarding, by the ED notification component 208, to the server device 122. For example, the server device 122 can be associated with a remote medical monitoring service that can inform remote medical caregivers regarding the connectivity problem between the implantable device 104 and the external device 116 based on reception of the notification from the ED notification component 208.

In some embodiments, the external device 116 and/or the implantable device 104 can be reconfigured to correct an identified telemetry connectivity problem between the external device 116 and the implantable device 104 (e.g., as identified via the ID connectivity assessment component 406, the external device 116 via the ED connectivity assessment component 206, and/or the server device 122 via SD connectivity assessment component 606, discussed infra with respect to FIG. 6). According to these embodiments, the implantable device 104 can include ID configuration component 412 to facilitate reconfiguring the external device 116 and/or the implantable device 104 to correct the telemetry connectivity problem.

The ID configuration component 412 can perform same or similar functions as the ED configuration component 212. For example, in one embodiment, the ID configuration component 412 is configured to apply reconfiguration information received from the external device 116. According to this embodiment, the external device 116 or the server device 122 can determine how to reconfigure the implantable device 104 to correct an identified telemetry connectivity problem between the implantable device 104 and the external device 116. The external device 116 or the server device 122 (e.g., using the external device 116 as a relay) can further send the implantable device reconfiguration information that includes instructions regarding how implantable device 104 should be reconfigured. The implantable device 104 can also receive a command from the external device 116 in association with reception of the reconfiguration information that instructs the implantable device to apply the reconfiguration information. In response to reception of the reconfiguration information and the command from the external device 116, ID configuration component 412 can apply the reconfiguration information.

In additional embodiments, in response to a determination (e.g., by the ID connectivity assessment component 406) that a connectivity problem between the external device 116 and the implantable device 104 is based on telemetry communication protocol configuration settings of the external device 116 and/or the implantable device 104, the ID configuration component 412 can update one or more configuration settings of the implantable device 104.

For example, the ID configuration component 412 can modify a number of data packets per connection interval that the external device 116 should send to the implantable device 104 and/or a number of data packets per connection interval that the implantable device 104 should send the external device 116. In another example, the ID configuration component 412 can change the duration of for which the implantable device 104 and the external device 116 should maintain a connection in association with an established telemetry session (i.e., modify the connection interval).

For example, the external device 116 (e.g., via ED connectivity assessment component 206) or the server device 122 (e.g., via SD connectivity assessment component 606) can determine that a connectivity error condition associated with telemetry communication between the implantable device 104 and the external device 116 exists based on a determination that an amount of advertisement signals received by the external device 116 from the implantable device 104 within a defined time period is below a threshold amount. The external device 116 or the server device 122 can further determine one or more operations to correct the connectivity error condition that involves reconfiguration of a telemetry communication protocol employed by the implantable device 104. The external device 116 or the server device 122 (e.g., using the external device 116 as a relay) can further transmit reconfiguration information to the implantable device 104 that instructs the implantable device 104 to reconfigure the telemetry communication protocol setting accordingly. The ID configuration component 412 can receive the reconfiguration information and reconfigure the communication protocols employed by the implantable device 104 accordingly.

The ID configuration component 412 can further automatically update telemetry communication protocol parameters employed by the implantable device 104 and/or the external device 116 based on the operations determined to correct the telemetry communication protocols employed by the respective devices. For example, the ID configuration component 412 can direct the implantable device 104 to update its telemetry communication protocol settings to increase a connection interval between the external device 116 and the implantable device 104. Including, but not limited to, updating the telemetry communication protocols employed by the external device 116, the ID configuration component 412 can send the external device 116 reconfiguration information that defines how the external device 116 should update its telemetry communication protocol parameters. The reconfiguration information can further direct the external device to apply the reconfiguration information to update its telemetry protocol settings.

FIG. 6 illustrates a block diagram of an example, non-limiting server device (e.g., server device 122) in accordance with one or more embodiments described herein. The server device 122 includes server device (SD) communication component 602, SD connectivity monitoring component 604, SD connectivity assessment component 606, SD notification component 608 and SD configuration component 610. In some embodiments, the respective components of server device 122 can perform same or similar functions as the corresponding external device 116 components. For example, the SD communication component 602 can perform same or similar functions as the ED communication component 202, the SD connectivity monitoring component 604 can perform same or similar functions as the ED connectivity monitoring component 204, the SD connectivity assessment component 606 can perform same or similar functions as the ED connectivity assessment component 206, the SD notification component 608 can perform same or similar functions as the ED notification component 208, and the SD configuration component 610 can perform same or similar functions as the ED configuration component 212.

One or more of the components of the server device 122 constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The server device 122 can include SD memory 614 configured to store the computer executable components and instructions, and SD processor 616 to facilitate operation of the computer executable components and instructions by the sever device 122. The external server device 122 can include a SD bus 618 that couples the various components of the SD, including, but not limited to, the SD communication component 602, the SD connectivity monitoring component 604, the SD connectivity assessment component 606, the SD notification component 608, the SD configuration component 612, the SD processor 216 and/or the SD memory 614. Repetitive description of like elements employed in other embodiments described herein is omitted for sake of brevity.

With reference to FIGS. 1 and 6, the SD communication component 602 is configured to facilitate communication between the server device 122 and the external device 116 using various communication protocols and networks discussed with reference to FIG. 1 and communication link 120. For example, the SD communication component 602 can facilitate telemetry communication between the server device 122 and the external device 116 using a wide-range wireless telemetry communication protocol such as an IP or cellular based communication protocol via a WAN. In another embodiment, the SD communication component 602 can facilitate communication between the external device 116 and the server device 122 via a LAN (e.g., using a Wi-Fi based communication protocol) or a wired connection.

Similar to ED connectivity monitoring component 204 and ID connectivity monitoring component 404, the SD connectivity monitoring component 604 is configured to monitor information associated with the integrity and quality of telemetry connectivity between the external device 116 and the implantable device 104, (i.e., telemetry connectivity information). In particular, the SD connectivity monitoring component 604 can monitor or track telemetry connectivity information regarding telemetry connectivity between the external device 116 and the implantable device 104 provided to the server device 122 from the external device 116 and/or the implantable device 104. For example, in some embodiments, the external device 116 is configured to send (e.g., via ED reporting component 210) the server device 122 telemetry connectivity information monitored by the ED connectivity monitoring component 204. In other embodiments, the external device 116 is configured to send the server device 122 telemetry connectivity information monitored by the ID connectivity monitoring component 404 based on provision of the telemetry connectivity information to the external device 116 by the implantable device 104 (e.g., via ID reporting component 410). According to these embodiments, the SD connectivity monitoring component 604 can monitor or log the telemetry connectivity information received from the external device 116.

The SD connectivity assessment component 606 is configured to evaluate received telemetry connectivity information in a same or similar fashion described with respect to ED connectivity assessment component 206 and/or ID connectivity assessment component 406. In particular, the SD connectivity assessment component 606 can evaluate the integrity and/or quality of telemetry connectivity between the external device 116 and the implantable device 104 based on the received telemetry connectivity information monitored by the ED connectivity monitoring component 204 and/or the ID connectivity monitoring component 404. In accordance with various embodiments, the SD connectivity assessment component 606 can analyze the telemetry connectivity information to determine whether a telemetry connectivity error condition exists between the external device 116 and the implantable device 104.

For example, in one exemplary embodiment, the SD connectivity assessment component 606 can analyze telemetry connectivity information including advertisement signal information regarding amount, timing and/or frequency of advertisement signals received by the external device 116 from the implantable device 104 and/or amount, timing and/or frequency of advertisement signals sent by the implantable device 104 to the external device 116. For example, the SD connectivity assessment component 606 can determine that a telemetry connectivity error condition associated with performance of telemetry communication between the external device 116 and the implantable device 104 exists based on an amount of advertisement signals received by the external device 116 within a defined period of time being less than a threshold amount. In another example, the SD connectivity assessment component 606 can determine that a telemetry connectivity error condition exists based on an amount of advertisement signals transmitted by the implantable device 104 within a defined period of time is less than a threshold amount. In another example, the SD connectivity assessment component 606 can determine that a telemetry connectivity error condition exists based on a degree of incongruency between an amount of advertisement signals transmitted by the implantable device 104 to the external device 116 and another amount of advertisement signals received by the external device 116 from the implantable device.

In another exemplary embodiment, the SD connectivity assessment component 606 can analyze telemetry connectivity information regarding amount, timing and/or frequency of successful telemetry connectivity sessions established between the implantable device 104 and the external device 116 (e.g., as logged by the external device 116 and/or the implantable device 104). For example, the SD connectivity assessment component 606 can determine that a telemetry connectivity error condition associated with performance of telemetry communication between the external device 116 and the implantable device 104 exists based on the amount of successful telemetry sessions that occurred over a period of time being below a threshold value. In another example, the SD connectivity assessment component 606 can determine that a telemetry connectivity error condition exists based on discrepancy between the amount of successful telemetry sessions identified by the external device 116 over a period of time and another amount of successful telemetry sessions identified be the implantable device over the period of time. In another example, the SD connectivity assessment component 606 can determine that a telemetry connectivity error condition exists based on ratio representative of successful telemetry sessions established between the external device 116 and the implantable device 104 and an amount of advertisement signals received or transmitted by the respective devices, being less than a threshold ratio.

Still in other exemplary embodiments, the SD connectivity assessment component 606 can analyze interrogation success rate information, RSSI information for the external device 116 and/or the implantable device 104, and throughput information for the external device 116 and the implantable device 104 to identify and/or diagnose telemetry connectivity problems between the respective devices (e.g., in accordance with the techniques described with respect to ED connectivity assessment component 206 and ID connectivity assessment component 406).

Similar to ED notification component 208, the SD notification component 608 facilitates notifying users regarding a telemetry connectivity problem determined to exist between the external device 116 and the implantable device 104. In one embodiment, the SD notification component 608 is configured to generate a notification based on a determination that a telemetry connectivity problem exists between the external device 116 and the implantable device 104. The notification can include information indicating the implantable device 104 and the external device 116 are experiencing a telemetry connectivity problem. In some embodiments, the notification can also include information identifying a cause of the telemetry connectivity problem. The SD notification component 608 can further render the notification at the server device 122 and/or send the notification to another device. For example, the SD notification component 608 can send (e.g., using SD communication component 602), the notification to the external device 116 for rendering at the external device. The SD notification component 608 can also send the notification to the implantable device 104 (e.g., using the external device 116 as a relay), and/or send the notification to other suitable devices.

In some embodiments, the external device 116 and/or the implantable device 104 can be reconfigured to correct a telemetry connectivity error condition identified between the external device 116 and the implantable device 104. In some implementations, the SD configuration component 610 is configured to facilitate reconfiguring the external device 116 and/or the implantable device 104 to correct the telemetry connectivity problem. For example, the SD configuration component 610 can determine how to update the configuration settings of one or both of the devices to correct the connectivity problem. In particular, the SD configuration component 610 can determine a modification to one or more telemetry communication protocol parameters employed by the external device 116 and/or the implantable device 104 that corrects the connectivity problem. For example, the SD configuration component 610 can modify a number of data packets per connection interval that the external device 116 should send to the implantable device 104 and/or a number of data packets per connection interval that the implantable device 104 should send the external device 116. In another example, the SD configuration component 610 can change the duration of for which the implantable device 104 and the external device 116 should maintain a connection in association with an established telemetry session (i.e., modify the connection interval).

In one embodiment, the SD configuration component 610 can also send the external device 116 a command including reconfiguration information and that instructs the external device 116 to reconfigure one or more parameters of the telemetry communication protocol parameters employed by the external device 116. Based on reception of the command, the external device 116 can reconfigure its telemetry communication protocol parameters according to the reconfiguration information. In another implementation, the SD configuration component 610 can send the external device 116 a command including reconfiguration information directed to the implantable device 104. The command can instruct the external device 116 to send the reconfiguration information to the implantable device 104. Based on reception of the command, the external device 116 can send the reconfiguration information to the implantable device 104 and based on reception of the command from the external device 116, the implantable device 104 can reconfigure its telemetry communication protocol parameters according to the reconfiguration information.

FIGS. 7-11 illustrate flow diagrams of example, non-limiting methods for monitoring integrity of telemetry connectivity between an implantable device and an external device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts can be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 7:
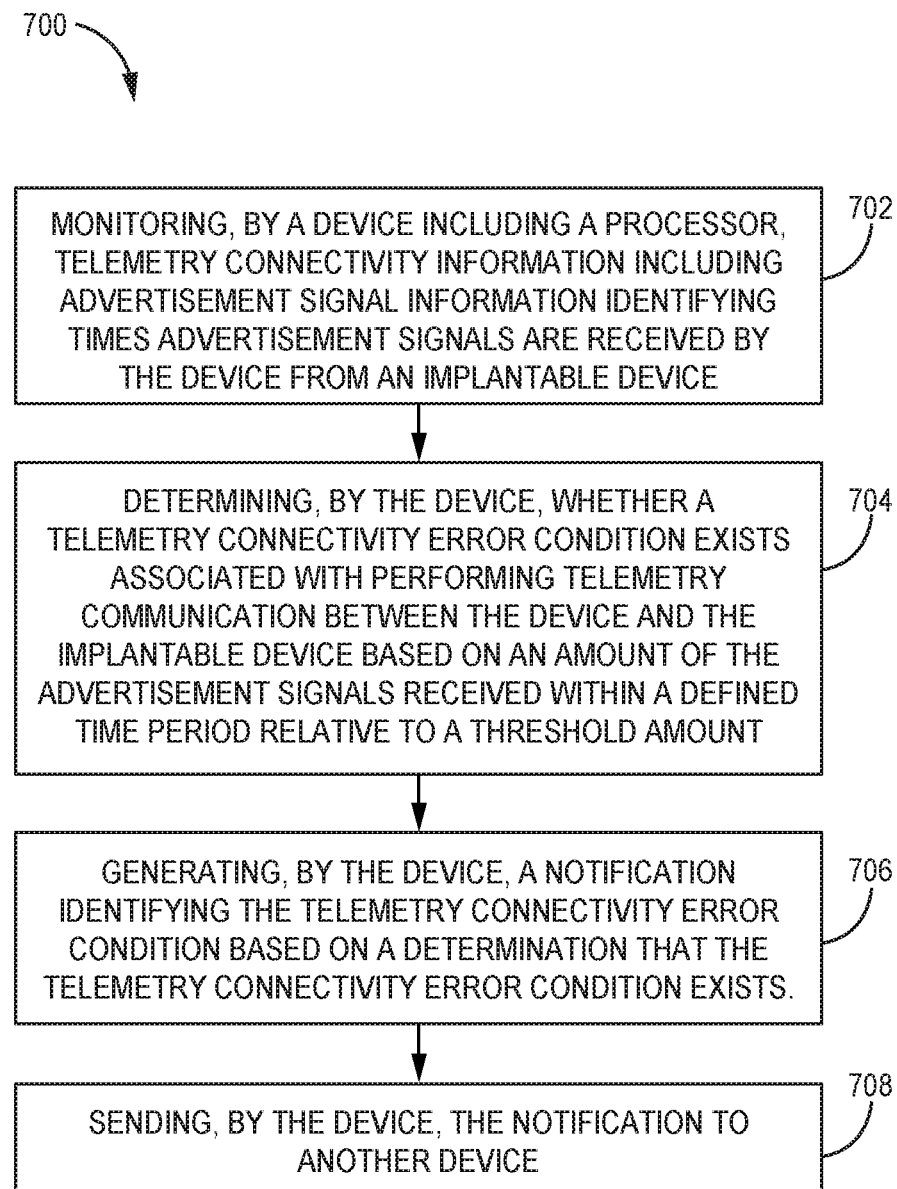
FIGS. 7-11 illustrate flow diagrams of example, non-limiting methods for monitoring integrity of telemetry connectivity between an implantable device and an external device in accordance with one or more embodiments described herein.

Referring now to FIG. 7, shown is a flow diagram of an example method 700 for monitoring integrity of telemetry connectivity between an implantable device and an external device in accordance with one embodiment. Various embodiments of method 700 can be performed by a device including a processor, such as external device 116. In some embodiments of method 700, external device 116 employs ED communication component 202, ED connectivity monitoring component 204, ED connectivity assessment component 206 and/or ED notification component 208. Repetitive description of like elements employed in other embodiments described herein is omitted for sake of brevity.

At 702, a device including a processor (e.g., external device 116), monitors telemetry connectivity information including advertisement signal information identifying times advertisement signals are received by the device from an implantable device (e.g., implantable device 104). At 704, the device determines whether a telemetry connectivity error condition exists associated with performing telemetry communication between the device and the implantable device based on an amount of the advertisement signals received within a defined time period relative to a threshold amount. At 706, the device generates a notification identifying the telemetry connectivity error condition based on a determination that the telemetry connectivity error condition exists. For example, in one embodiment, the device determines that the telemetry connectivity error exists based on the amount of the advertisement signals received within the defined time period being below the threshold amount. At 708, the device sends the notification to another device. For example, the device can send the notification to a server device (e.g., server device 122) and/or the implantable device (e.g., implantable device 104). In other embodiments, the device can render the notification at the device.

Figure 8:
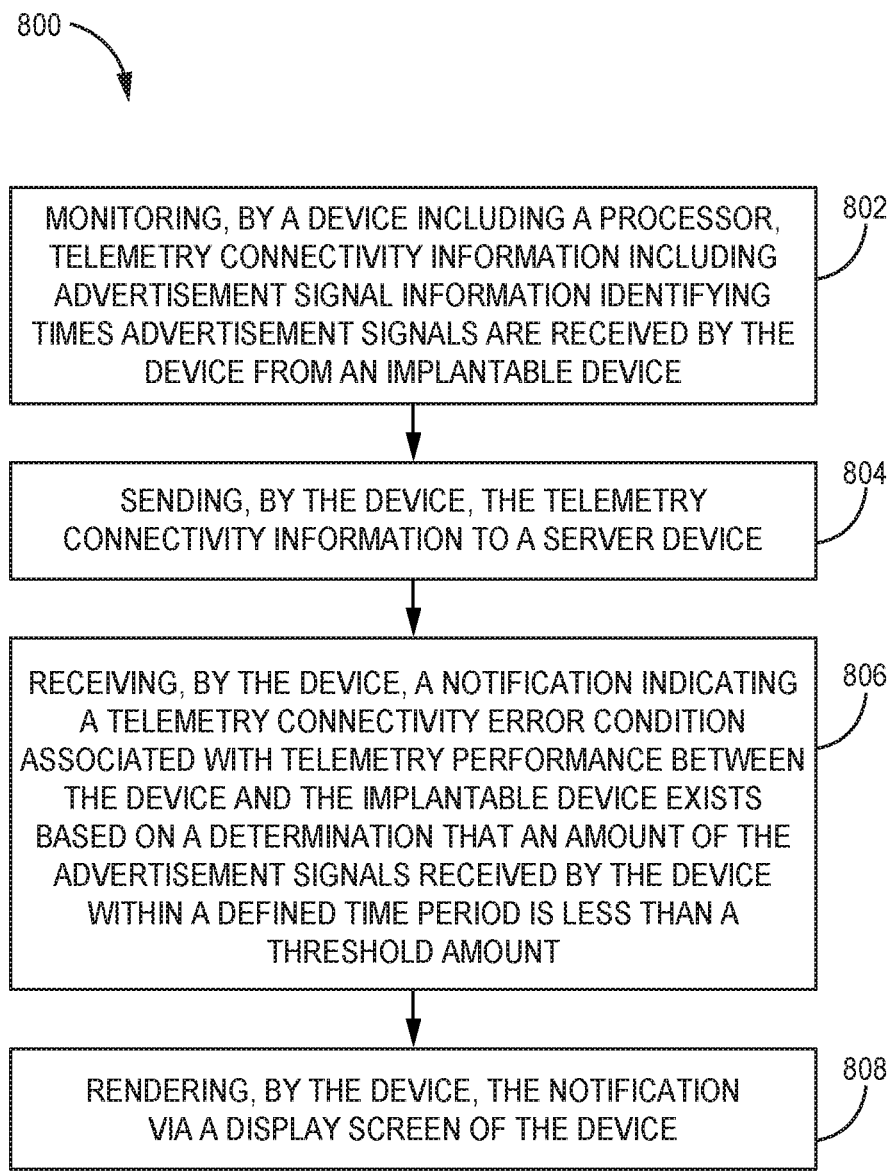

Turning now to FIG. 8, shown is a flow diagram of another example method 800 for monitoring integrity of telemetry connectivity between an implantable device and an external device in accordance with one embodiment. Various embodiments of method 800 can be performed by a device including a processor, such as external device 116. In some embodiments of method 800, external device 116 employs ED communication component 202, ED connectivity monitoring component 204, ED notification component 208 and/or ED reporting component 210. Repetitive description of like elements employed in other embodiments described herein is omitted for sake of brevity.

At 802, a device including a processor (e.g., external device 116), monitors telemetry connectivity information including advertisement signal information identifying times advertisement signals are received by the device from an implantable device (e.g., implantable device 104). At 804, the device sends the telemetry connectivity information to a server device (e.g., server device 122). At 806, the device receives a notification indicating a telemetry connectivity error condition associated with telemetry performance between the device and the implantable device exists based on a determination (e.g., made by the server device 122) that an amount of the advertisement signals received by the device within a defined time period is less than a threshold amount. At 808, the device renders the notification via a display of the device.

Figure 9:
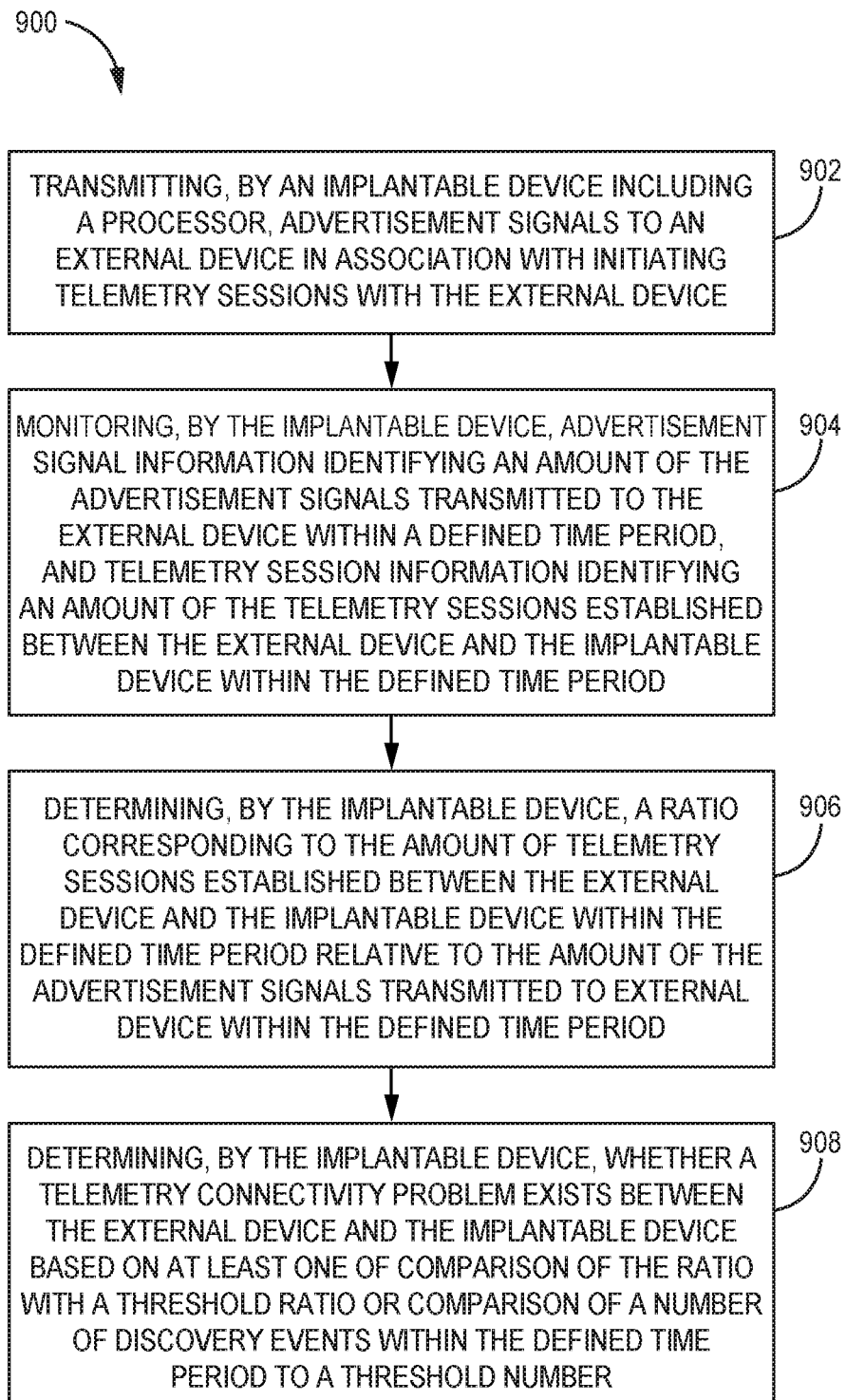

FIG. 9 shows a flow diagram of another example method 900 for monitoring integrity of telemetry connectivity between an implantable device and an external device in accordance with one embodiment. Various embodiments of method 900 can be performed by an implantable device including a processor, such as implantable device 104. In some embodiments of method 900, implantable device 104 employs ID communication component 402, ID connectivity monitoring component 404, ID connectivity assessment component 406 and/or ID notification component 408. Repetitive description of like elements employed in other embodiments described herein is omitted for sake of brevity.

At 902, an implantable device including a processor (e.g., implantable device 104) transmits advertisement signals to an external device in association with initiating telemetry sessions with the external device. At 904, the implantable device monitors advertisement signal information identifying an amount of the advertisement signals transmitted to the external device within a defined time period. The implantable device also monitors telemetry session information identifying an amount of the telemetry sessions established between the external device and the implantable device within the defined time period. At 906, the implantable device determines a ratio corresponding to the amount of telemetry sessions established between the external device and the implantable device within the defined time period relative to the amount of the advertisement signals transmitted to the external device within the defined time period. At 908, the device determines whether a telemetry connectivity problem exists between the external device and the implantable device based on at least one of comparison of the ratio with a threshold ratio or comparison of a number of discovery events within the defined time period to a threshold number. For example, the implantable device can determine that the telemetry connectivity problem exists based on the ratio being less than the threshold ratio. In another example, the implantable device can determine that the telemetry connectivity problem exists based on the number of discovery events being below the threshold number.

Figure 10:
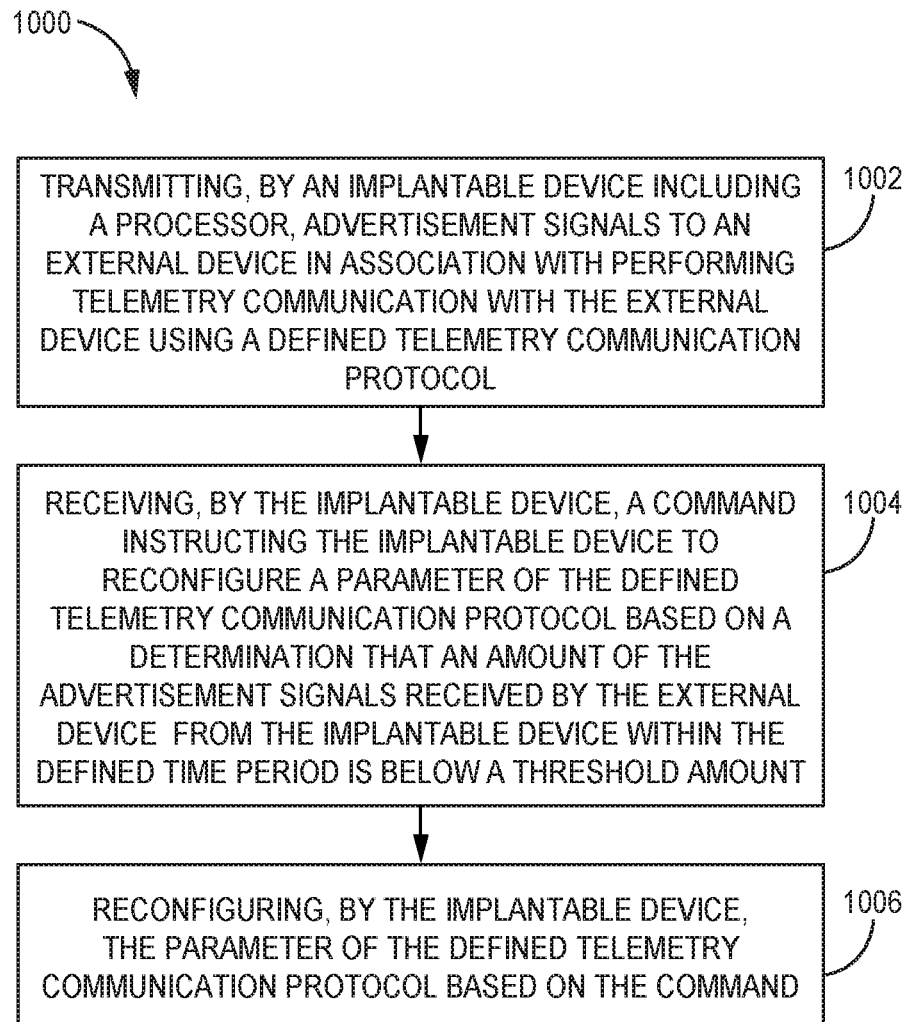

FIG. 10 shows a flow diagram of another example method 1000 for monitoring integrity of telemetry connectivity between an implantable device and an external device in accordance with one embodiment. Various embodiments of method 1000 can be performed by an implantable device including a processor, such as implantable device 104. In some embodiments of method 1000, implantable device 104 employs ID communication component 402 and/or ID configuration component 412. Repetitive description of like elements employed in other embodiments described herein is omitted for sake of brevity.

At 1002, an implantable device including a processor (e.g., implantable device 104), transmits advertisement signals to an external device in association with performing telemetry communication with the external device using a defined telemetry communication protocol (e.g., a BLE based communication protocol). At 1004, the implantable device receives a command instructing the implantable device to reconfigure a parameter of the defined telemetry communication protocol based on a determination (e.g., made via ED connectivity assessment component 206 or SD connectivity assessment component 606) that an amount of the advertising signals received by the external device from the implantable device within the defined time period is below a threshold amount. At 1006, the implantable device reconfigures the parameter of the defined telemetry communication protocol based on the command.

Figure 11:
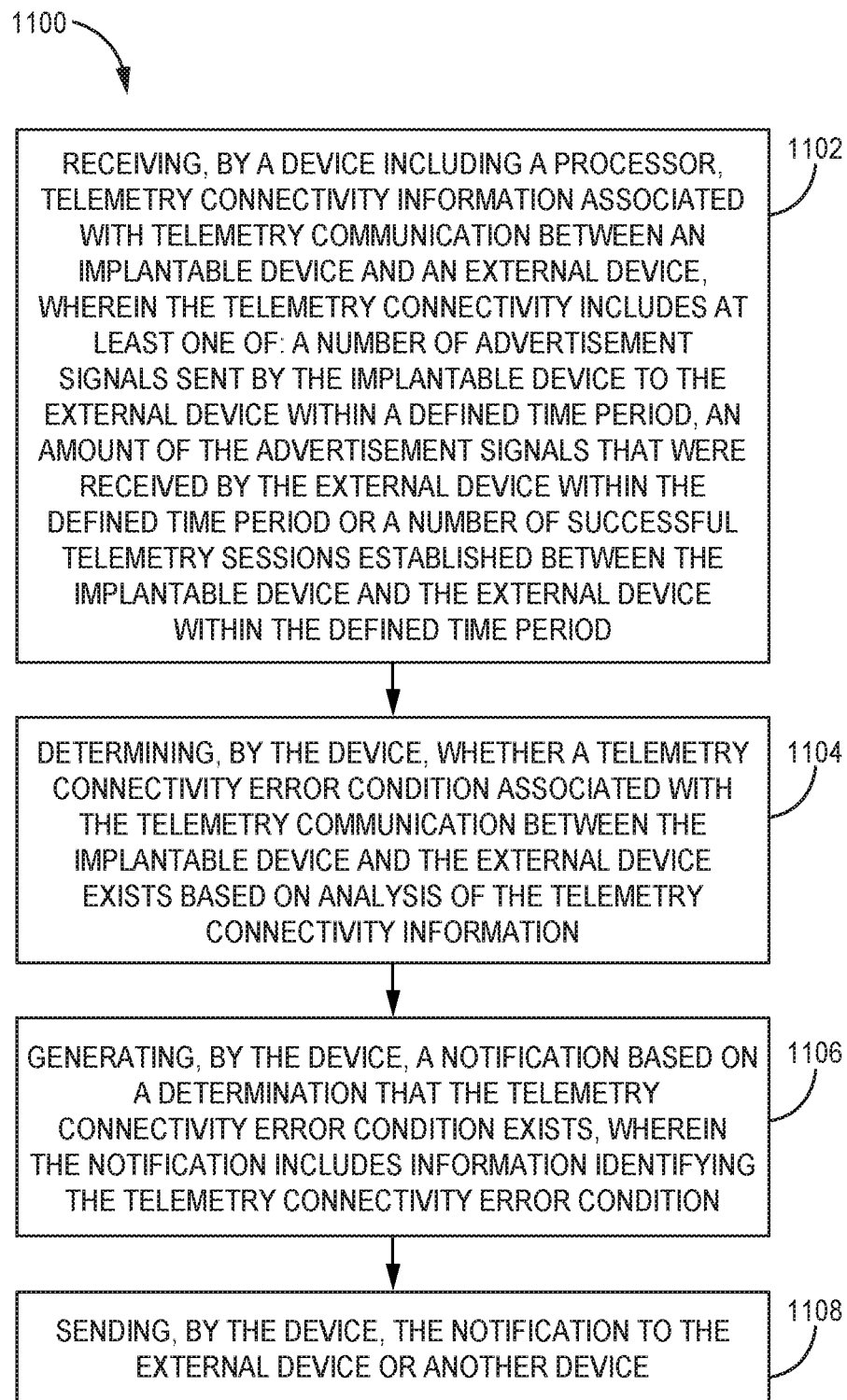

FIG. 11 shows a flow diagram of another example method 1100 for monitoring integrity of telemetry connectivity between an implantable device and an external device in accordance with one embodiment. Various embodiments of method 1100 can be performed by a device including a processor, such as server device 122. In some embodiments of method 1100, server device 122 employs SD communication component 602, and SD configuration component 610. Repetitive description of like elements employed in other embodiments described herein is omitted for sake of brevity.

At 1102, a device including a processor (e.g., server device 122), receives telemetry connectivity information associated with telemetry communication between an implantable device (e.g., implantable device 104) and an external device (e.g., external device 116). The telemetry connectivity information includes at least one of: a number of advertisement signals sent by the implantable device to the external device within a defined time period, an amount of the advertisement signals that were received by the external device within the defined time period or a number of successful telemetry sessions established between the implantable device and the external device within the defined time period. At 1104, the device determines whether a telemetry connectivity error condition associated with the telemetry communication between the implantable device and the external device exists based on analysis of the telemetry connectivity information. For example, the device can determine that a telemetry connectivity error condition exists based on a miscorrelation between the number of advertisement signals sent by the implantable device to the external device within a defined time period, the amount of the advertisement signals that were received by the external device within the defined time period, and/or the number of successful telemetry sessions established between the implantable device and the external device within the defined time period. At 1106, the device generates a notification base on a determination that the telemetry connectivity error condition exists. The notification can include information identifying the telemetry connectivity error condition. At 1108, the device sends the notification to the external device or another device.

Figure 12:
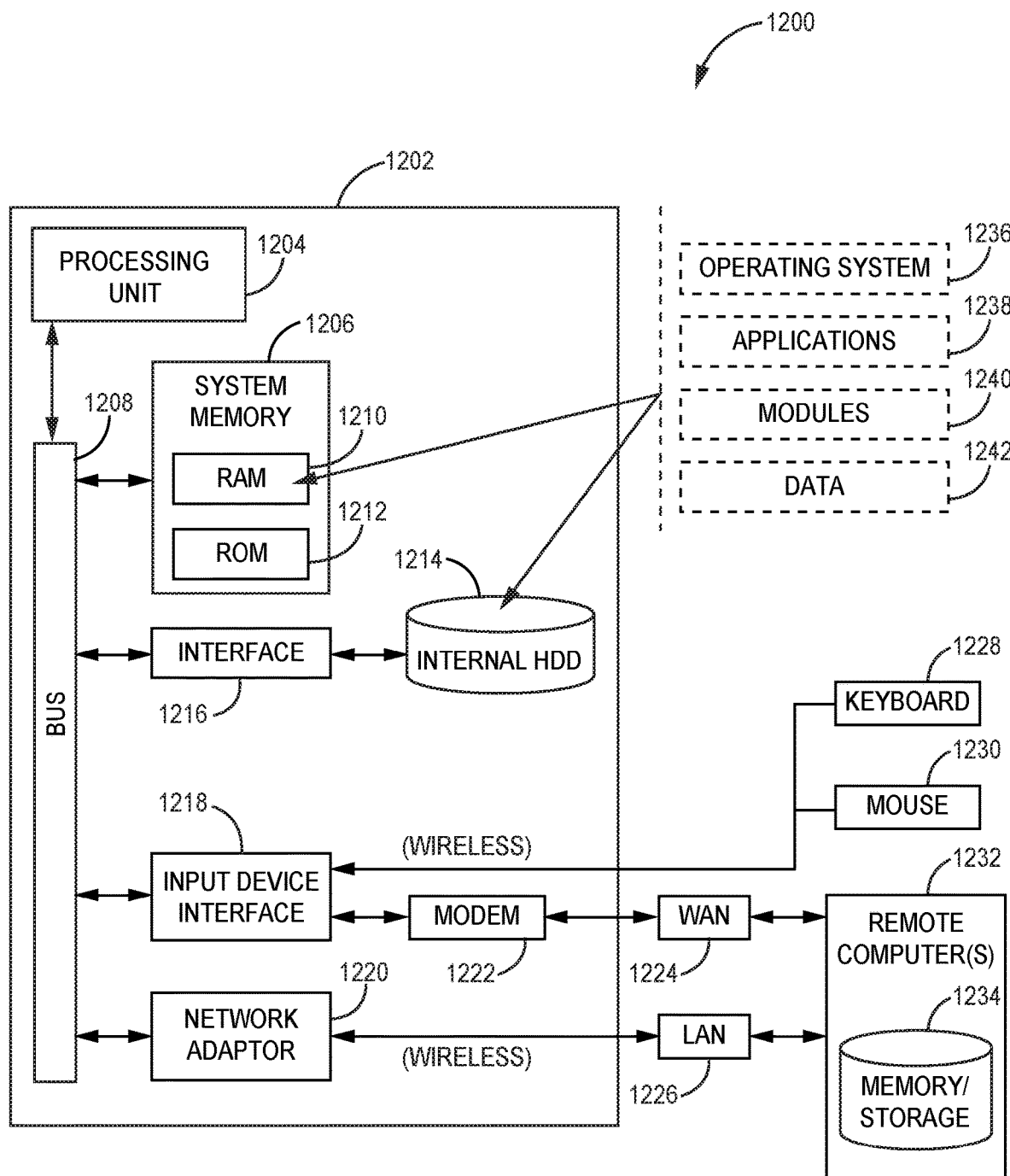
FIG. 12 illustrates a block diagram of an example, non-limiting computer operable to facilitate monitoring the integrity of telemetry connectivity between an implantable device and an external device in accordance with one or more embodiments described herein.

FIG. 12 illustrates a block diagram of a computer operable to facilitate communication between an implantable device and an external device in accordance with one or more embodiments described herein. For example, in some embodiments, the computer can be or be included within implantable device 104 and/or external device 116. Repetitive description of like elements employed in other embodiments described herein is omitted for sake of brevity. Including, but not limited to, provide additional context for one or more embodiments described herein, FIG. 12 and the following discussion are intended to provide a brief, general description of a suitable computing environment 1200 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, example environment 1200 that can be employed to implement one or more embodiments of the embodiments described herein includes computer 1202. Computer 1202 includes processing unit 1204, system memory 1206 and system bus 1208. System bus 1208 couples system components including, but not limited to, system memory 1206 to processing unit 1204. Processing unit 1204 can be any of various commercially available processors. Dual microprocessors and other multiprocessor architectures can also be employed as processing unit 1204.

System bus 1208 can be any of several types of bus structure that can further interconnect to a memory bus (with or without a memory controller), a peripheral bus, and a local bus using any of a variety of commercially available bus architectures. System memory 1206 includes RAM 1210 and ROM 1212. A basic input/output system (BIOS) can be stored in a non-volatile memory such as ROM, erasable programmable read only memory (EPROM), EEPROM, which BIOS contains the basic routines that help to transfer information between elements within computer 1202, such as during startup. RAM 1210 can also include a high-speed RAM such as static RAM for caching data.

Computer 1202 further includes internal hard disk drive (HDD) 1214 (e.g., Enhanced Integrated Drive Electronics (EIDE), Serial Advanced Technology Attachment (SATA)). HDD 1214 can be connected to system bus 1208 by hard disk drive interface 1216. The drives and their associated computer-readable storage media provide nonvolatile storage of data, data structures, computer-executable instructions, and so forth. For computer 1202, the drives and storage media accommodate the storage of any data in a suitable digital format.

A number of program modules can be stored in the drives and RAM 1210, including operating system 1236, one or more application programs 1238, other program modules 1240 and program data 1242. All or portions of the operating system, applications, modules, and/or data can also be cached in RAM 1210. The systems and methods described herein can be implemented utilizing various commercially available operating systems or combinations of operating systems.

A mobile device can enter commands and information into computer 1202 through one or more wireless input devices, e.g., wireless keyboard 1228 and a pointing device, such as wireless mouse 1230. Other input devices (not shown) can include a smart phone, tablet, laptop, wand, wearable device or the like. These and other input devices are often connected to the processing unit 1204 through input device interface 1218 that can be coupled to system bus 1208, but can be connected by other interfaces, such as a parallel port, an IEEE serial port, a game port and/or a universal serial bus (USB) port.

Computer 1202 can operate in a networked environment using logical connections via wired and/or wireless communications to one or more remote computers, such as remote computer(s) 1232. Remote computer(s) 1232 can be a workstation, a server computer, a router, a personal computer, portable computer, microprocessor-based entertainment appliance, a peer device or other common network node, and typically includes many or all of the elements described relative to computer 1202, although, for purposes of brevity, only memory/storage device 1234 is illustrated. The logical connections depicted include wired/wireless connectivity to a local area network (LAN) 1226 and/or larger networks, e.g., WAN 1224, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1202 can be connected to local network through a wired and/or wireless communication network interface or adapter 1220. Adapter 1220 can facilitate wired or wireless communication to LAN 1226, which can also include a wireless access point (AP) connected to the LAN 1226 for communicating with adapter 1220.

When used in a WAN networking environment, computer 1202 can include modem 1222 or can be connected to a communications server on WAN 1224 or has other means for establishing communications over WAN 1224, such as by way of the Internet. Modem 1222, which can be internal or external and a wired or wireless device, can be connected to system bus 1208 via input device interface 1218. In a networked environment, program modules depicted relative to computer 1202 or portions thereof, can be stored in a remote memory/storage device. It will be appreciated that the network connections shown are example and other means of establishing a communications link between the computers can be used.

Computer 1202 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 12 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)=confidence$ (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a defined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, including, but not limited to, optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A device comprising:
   a memory that stores executable components; and
   a processor that executes the executable components stored in the memory, wherein the executable components comprise:
   a monitoring component configured to monitor advertisement signal information identifying an amount of advertisement signals transmitted from the device to a second device within a defined time period, or telemetry session information identifying an amount of telemetry sessions that are established between the second device and the device within the defined time period; and
   a connectivity assessment component configured to determine whether a telemetry connectivity problem exists between the second device and the device based on at least one of a number of discovery events within the defined time period or a ratio corresponding to the amount of telemetry sessions that are established between the second device and the device within the defined time period relative to the amount of the advertisement signals transmitted to the second device within the defined time period.

2. The device of claim 1, wherein the connectivity assessment component is configured to determine that the telemetry connectivity problem exists between the second device and the device based on at least one of the number of discovery events being less than a threshold number or the ratio being less than a threshold ratio.

3. The device of claim 2, further comprising:
   a notification component configured to generate a notification indicating the telemetry connectivity problem exists between the second device and the device based on a determination that at least one of the number of discovery events is below the threshold number or the ratio is below the threshold ratio, and wherein the notification component is further configured to send the notification to the second device for at least one of rendering at the second device or relaying, by the second device, to another device.

4. The device of claim 1, further comprising a reporting component configured to send the advertisement signal information to the second device.

5. The device of claim 1, further comprising:
   a configuration component configured to receive a command instructing the device to reconfigure a telemetry communication protocol employed by the device to communicate with the second device based on a determination that an amount of the advertisement signals that are received by the second device from the device within the defined time period is below a threshold amount.

6. The device of claim 5, wherein the configuration component is configured to receive the command from the second device and wherein the command originated from a server device that is separate from the second device.

7. The device of claim 1, wherein the monitoring component is further configured to monitor interrogation signal information identifying an amount of interrogation signals received from the second device within the defined time period, and wherein the connectivity assessment component is further configured to determine that the telemetry connectivity problem exists between the second device and the device based on the amount of interrogation signals received being below a threshold amount.

8. The device of claim 1, wherein the monitoring component is further configured to monitor interrogation signal information identifying an amount of interrogation signals received from the second device within the defined time period, and wherein the connectivity assessment component is further configured to determine that the telemetry connectivity problem exists between the second device and the device based on a second ratio, corresponding to the amount of interrogation signals received within the defined time period relative to the amount of telemetry sessions established between the second device and the device within the defined time period, being less than a threshold ratio.

9. The device of claim 1, wherein the monitoring component is further configured to monitor signal strength information identifying strengths of signals received from the second device within the defined time period, and wherein the connectivity assessment component is further configured to determine that the telemetry connectivity problem exists between the second device and the device based on an average strength of the strengths of the signals received being less than a threshold amount.

10. The device of claim 1, wherein the monitoring component is further configured to monitor signal strength information identifying strengths of signals received from the second device within the defined time period, and wherein the connectivity assessment component is further configured to determine that the telemetry connectivity problem exists between the second device and the device based on a degree of variance in the strengths of the signals received exceeding a threshold degree of variance.

11. The device of claim 1, wherein the monitoring component is further configured to monitor throughput information identifying throughput of data packets received from the second device within the defined time period, and wherein the connectivity assessment component is further configured to determine that the telemetry connectivity problem exists between the second device and the device based on the throughput being less than a threshold amount.

12. The device of claim 1, wherein the monitoring component is further configured to monitor throughput information identifying throughput of data packets transmitted by the device to the second device within the defined time period, and wherein the connectivity assessment component is further configured to determine that the telemetry connectivity problem exists between the second device and the device based on throughput being less than a threshold amount.

13. The device of claim 1, wherein the device further comprises a communication component configured to transmit the advertisement signals to the second device using a BLUETOOTH® Low Energy communication protocol.

14. A method, comprising:
   monitoring, by a device comprising a processor, advertisement signal information identifying an amount of advertisement signals transmitted from the device to a second device within a defined time period, or telemetry session information identifying an amount of telemetry sessions that are established between the second device and the device within the defined time period;
   determining, by the device, whether a telemetry connectivity problem exists between the second device and the device based on at least one of a number of discovery events within the defined time period or a ratio corresponding to the amount of telemetry sessions that are established between the second device and the device within the defined time period relative to the amount of the advertisement signals transmitted to the second device within the defined time period.

15. The method of claim 14, wherein the determining comprises determining that the telemetry connectivity error condition exists based on at least one of the number of discovery events being less than a threshold number or the ratio being less than a threshold ratio.

16. The method of claim 14, further comprising;
generating a notification indicating the telemetry connectivity problem exists between the second device and the device based on a determination that at least one of the number of discovery events is below the threshold number or the ratio is below the threshold ratio; and
sending the notification to the second device for at least one of rendering at the second device or relaying, by the second device, to another device.

17. The method of claim 14, further comprising sending the advertisement signal information to the second device.

18. The method of claim 14, further comprising receiving a command instructing the device to reconfigure a telemetry communication protocol employed by the device to communicate with the second device based on a determination that an amount of the advertisement signals that are received by the second device from the device within the defined time period is below a threshold amount.

19. The method of claim 18, wherein the command is received from the second device and wherein the command originated from a server device that is separate from the second device.

20. A non-transitory computer-readable storage medium storing instructions, which when executed by one or more processors cause the one or more processors to:
monitor advertisement signal information identifying an amount of advertisement signals transmitted from the device to a second device within a defined time period, or telemetry session information identifying an amount of telemetry sessions that are established between the second device and the device within the defined time period; and
determine whether a telemetry connectivity problem exists between the second device and the second device based on at least one of a number of discovery events within the defined time period or a ratio corresponding to the amount of telemetry sessions that are established between the second device and the device within the defined time period relative to the amount of the advertisement signals transmitted to the second device within the defined time period.

* * * * *